US008092464B2

(12) United States Patent
McKay

(10) Patent No.: US 8,092,464 B2
(45) Date of Patent: Jan. 10, 2012

(54) SYRINGE DEVICES AND METHODS USEFUL FOR DELIVERING OSTEOGENIC MATERIAL

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1271 days.

(21) Appl. No.: 11/120,135

(22) Filed: Apr. 30, 2005

(65) Prior Publication Data
US 2008/0009823 A1 Jan. 10, 2008

(51) Int. Cl.
A61M 31/00 (2006.01)
(52) U.S. Cl. .......................................... 606/92; 604/218
(58) Field of Classification Search .................... 606/92, 606/93, 94, 99; 604/57, 59, 60, 103.1, 164.01, 604/166.01, 170.02, 218–243, 500
See application file for complete search history.

(56) References Cited

U.S. PATENT DOCUMENTS

| 4,013,078 | A | | 3/1977 | Feild |
| 5,439,464 | A | * | 8/1995 | Shapiro ............................ 606/83 |
| 5,562,736 | A | | 10/1996 | Ray et al. |
| 5,868,745 | A | | 2/1999 | Aleyne |
| 6,395,007 | B1 | | 5/2002 | Bhatnagar et al. |
| 6,413,278 | B1 | | 7/2002 | Marchosky |
| 6,454,767 | B2 | | 9/2002 | Alleyne |
| 6,524,296 | B1 | * | 2/2003 | Beals ............................. 604/500 |
| 6,541,037 | B1 | | 4/2003 | Lee et al. |
| 6,582,439 | B1 | * | 6/2003 | Sproul ............................. 606/92 |
| 6,592,559 | B1 | * | 7/2003 | Pakter et al. .................... 604/272 |
| 6,595,958 | B1 | * | 7/2003 | Mickley .................... 604/164.01 |
| 6,858,015 | B2 | | 2/2005 | List |
| 6,875,219 | B2 | * | 4/2005 | Arramon et al. ................. 606/92 |
| 7,175,629 | B2 | * | 2/2007 | Lin et al. ...................... 606/86 R |
| 7,507,243 | B2 | * | 3/2009 | Lambrecht et al. .............. 606/99 |
| 2001/0034527 | A1 | * | 10/2001 | Scribner et al. .................. 606/93 |
| 2001/0037091 | A1 | | 11/2001 | Wironen et al. |
| 2002/0010431 | A1 | * | 1/2002 | Dixon et al. .................... 604/221 |
| 2002/0026244 | A1 | | 2/2002 | Trieu |
| 2002/0049448 | A1 | | 4/2002 | Sand et al. |
| 2002/0082605 | A1 | * | 6/2002 | Reiley et al. ..................... 606/93 |
| 2002/0128636 | A1 | * | 9/2002 | Chin et al. ....................... 606/16 |
| 2002/0138145 | A1 | | 9/2002 | Marchosky |
| 2003/0004491 | A1 | | 1/2003 | Tenhuisen et al. |
| 2003/0069541 | A1 | * | 4/2003 | Gillis et al. ............... 604/164.01 |
| 2003/0125748 | A1 | * | 7/2003 | Li et al. ........................... 606/99 |
| 2003/0236573 | A1 | * | 12/2003 | Evans et al. ................ 623/23.58 |

(Continued)

FOREIGN PATENT DOCUMENTS
EP 0428378 5/1991
(Continued)

Primary Examiner — Thomas C. Barrett
Assistant Examiner — Christopher Beccia

(57) ABSTRACT

Described are syringe devices useful in delivering medical materials internally in patients. In certain embodiments, syringe devices of the invention include widening internal lumen to assist in effective delivery of substances therethrough, and/or curved barrel portions with curved lumens therein. In still further disclosed embodiments, syringe devices include adaptations to prevent compression of compressible carrier materials to be delivered therethrough, curved barrel portions with flexible plunger arms to track the curved barrel portions, barrel portions controllable in shape such as to introduce and remove curves, visible markings to denote the direction of deflection of syringe barrel portions, imagable markers located on the syringe barrel, a cooperating plunger apparatus, or both; or combinations of some or all of these features. Further described are spinal fusion procedures with syringe-based delivery of osteogenic material through a minimally invasive procedure, which procedures can utilize syringe devices of the invention.

29 Claims, 13 Drawing Sheets

U.S. PATENT DOCUMENTS

| | | | |
|---|---|---|---|
| 2004/0019311 A1* | 1/2004 | Crank et al. | 604/1 |
| 2004/0030345 A1* | 2/2004 | Aurin et al. | 606/92 |
| 2004/0034434 A1 | 2/2004 | Evans et al. | |
| 2004/0064193 A1 | 4/2004 | Evans et al. | |
| 2004/0127987 A1 | 7/2004 | Evans et al. | |
| 2004/0138758 A1 | 7/2004 | Evans et al. | |
| 2004/0254538 A1* | 12/2004 | Murphy et al. | 604/181 |
| 2005/0143688 A1* | 6/2005 | Lin et al. | 604/60 |
| 2007/0142842 A1* | 6/2007 | Krueger et al. | 606/92 |
| 2008/0091199 A1* | 4/2008 | Cragg | 606/60 |

FOREIGN PATENT DOCUMENTS

| | | |
|---|---|---|
| EP | 1477202 | 11/2004 |
| GB | 1584080 | 2/1981 |
| WO | WO 03/009884 | 2/2003 |
| WO | WO 2004/014263 | 2/2004 |

\* cited by examiner

SYRINGE DEVICES AND METHODS USEFUL FOR DELIVERING OSTEOGENIC MATERIAL

BACKGROUND

The present invention relates generally to medical devices and methods for delivering substances into patient tissues. In particular aspects, the invention relates to syringe-based devices and methods useful for the delivery of osteogenic materials into an interbody space between adjacent vertebra, for example to promote spinal fusion.

As further background, intervertebral discs, located between the endplates of adjacent vertebrae, stabilize the spine, distribute forces between vertebrae, and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

In certain instances, the only relief from the symptoms of these conditions is a discectomy, or surgical removal of a portion or all of an intervertebral disc, followed by fusion (arthrodesis) of the adjacent vertebrae. For these purposes, loadbearing implants are often sued to maintain the disc space while new bone growth and arthrodesis are achieved. A variety of such implants have been suggested and/or used, including hollow spinal cages that can be filled with osteogenic material, prior to insertion into the intervertebral space. Apertures defined in the cage communicate with the hollow interior to provide a path for tissue growth between the vertebral endplates. Interbody spinal implants fabricated from bone have also been employed. These include for instance threaded bone dowel products and impacted spacers. Again, an osteogenic substance can be implanted in conjunction with these spacers to achieve fusion.

Minimally-invasive spinal fusion procedures have been developed, including those involving anterior surgical approaches, e.g. using laproscopic instrumentation, and those involving posterior surgical approaches, e.g. using introducer sleeves. In these approaches, surgical access is provided to the interbody space through the cannulated device (e.g. laproscope or sleeve), and one or more loadbearing implants are introduced through the cannulated device. Oftentimes, the surgeon will pack an osteogenic graft material into an opening or recess in the loadbearing implant prior to introduction, to assist in the fusion process. Access to the surgical field in the interbody space can be somewhat limited in minimally invasive procedures. Nonetheless, techniques for implant and graft placement need to be conducted in a manner that ensures the opportunity for a positive surgical outcome.

In light of this background, there exist needs for improved and/or alternative devices, techniques and systems that are useful for the delivery of materials into an interbody space between adjacent vertebra. The present invention addresses these needs.

SUMMARY

In one aspect, the present invention provides a spinal fusion method that includes establishing a minimally invasive access to an interbody space between first and second adjacent vertebra of a patient. A loadbearing spinal implant is passed through the minimally invasive access and into the interbody space. A syringe device having an elongate syringe barrel and a distal delivery opening is manipulated so as to advance the elongate syringe barrel through the minimally invasive access and position its distal delivery opening within the interbody space. An osteogenic material is then delivered through the syringe barrel, out of the distal delivery opening, and into the interbody space. In certain embodiments, the inventive methods involve establishing access through a posterior access approach, or an anterior access approach. In either case, the access can include a cannulated member penetrating soft tissues of the patient and providing surgical access to the interbody space.

In another embodiment, the present invention provides a device useful for delivering an osteogenic graft material to an interbody space between first and second adjacent vertebra of a patient. The inventive device includes an elongate syringe barrel having an internal lumen communicating with an open distal end, wherein the open distal end is receivable within an interbody space between first and second adjacent vertebra of a patient. A compressible plug of porous osteogenic graft material is received in the lumen of the elongate syringe barrel and has a trailing end. A liquid pharmaceutical composition comprising an osteogenic protein is captured within pores of a compressible carrier to provide the osteogenic material. A plunger mechanism is provided, for applying force to the trailing end of the compressible plug to advance the plug through the lumen of the syringe barrel. Further, the syringe barrel, plug and plunger mechanism are configured wherein the plug is advanceable through the internal lumen with said plunger mechanism without substantial compression of the plug which thereby retains the liquid pharmaceutical composition within the plug. In certain embodiments, the syringe barrel has longitudinally extending lumen walls maintaining a substantially constant or increasing internal lumen cross-sectional area at least from a location corresponding to the trailing end of the graft material and extending to the open distal end.

In another embodiment, the present invention provides a syringe device useful for dispensing a medical material. The device includes a syringe barrel having an internal lumen. The barrel includes a receiving portion, a dispensing portion having an arcual shape, and a central portion connecting the receiving portion and dispensing portion. A material moving element is provided and is translatable within the barrel to move the material toward the dispensing portion. The material moving element includes a portion sufficiently flexible to adopt an arcual configuration to travel within at least a part of the arcual shape of the dispensing portion.

In another form, the invention provides a syringe device useful for delivering a medical material. The inventive device includes an elongate syringe barrel having an internal lumen and a distal end. The device includes at least one element cooperable with the syringe barrel to reposition its distal end, and in certain embodiments to selectively increase or decrease (including remove) a curvature of the syringe barrel. The syringe device, in some embodiments of the invention, also includes a plunger mechanism for advancing a medical material through the lumen of the syringe barrel.

In another aspect, the present invention provides a syringe device useful for delivering a medical material. The device includes an elongate syringe barrel with a distal barrel end having a distal delivery opening. A pushing element is provided having a leading end for contacting and advancing a medical substance through the lumen of the syringe barrel and out the distal delivery opening. One or more radiopaque or other similar imagable markers are provided on the syringe barrel and/or pushing element, in certain embodiments adjacent to (including at or near) the leading end of the pushing element, and/or adjacent to the distal barrel end.

In another embodiment, the present invention provides a syringe device useful for delivering a medical graft material susceptible to compression. The device includes a syringe barrel including a proximal end and a distal end. The syringe barrel has at least a barrel segment configured for passage of the medical graft material. The barrel segment includes an internal lumen terminating in a distal delivery opening, the internal lumen including at least a portion widening in a direction toward said distal delivery opening. The delivery opening has a delivery opening cross-sectional area at least as great as a minimum cross-sectional area of the barrel segment. A plunger mechanism translatable within the barrel segment and effective to transfer the medical material through the internal lumen and out of the delivery opening.

Another embodiment of the invention provides a syringe assembly useful for delivering an implant material. The assembly includes a syringe barrel having an internal lumen, a distal barrel end providing a distal delivery opening, and a proximal barrel end. The barrel further includes an arcual portion proximal to the distal end. The lumen of the barrel includes one or more regions of increasing cross-sectional area extending in a direction toward the distal barrel end, and the delivery opening has a delivery opening cross-sectional area at least as great as a minimum cross-sectional area of the syringe barrel. A material pushing element is provided operable to move the material through said lumen toward the distal end of said barrel.

In another embodiment, the invention provides a syringe assembly useful for dispensing material that includes a syringe barrel portion having an internal lumen and a plunger mechanism translatable within the barrel to move the material. The barrel portion further includes a funnel portion, a curved dispensing portion, and a central portion connecting the funnel portion and curved dispensing portion. The internal lumen includes one or more regions of increasing cross-sectional area in a direction from said central portion toward the curved dispensing portion, wherein the one or more widening regions are located at one or more of the central portion and the curved dispensing portion. The cross-sectional area of the internal lumen along a length of the barrel is at least as great as a cross-sectional area of the internal lumen where said funnel portion and the central portion connect. A plunger element is provided, at least a portion of which is operable to adopt a curved configuration to travel within said curved dispensing portion.

In a further embodiment, the present invention provides a syringe assembly useful for dispensing a medical material that includes an outer syringe barrel having a distal opening, and an inner tubular member received and advanceable within the outer syringe barrel, wherein the tubular member has a lumen for containing the medical material. A plunger element is provided having a plunger head received within the tubular member. The outer syringe barrel and tubular member are arranged wherein advancement of the tubular member within the outer syringe barrel is arrested when a distal tip of the tubular member is adjacent to or beyond the distal opening of the outer syringe barrel. The plunger element is then operable to expel the medical material from the lumen of the tubular member after advancement of the tubular member within the outer syringe barrel has been arrested.

In still further aspects, the present invention provides syringe devices as described above in combination with bone implant or grafting materials, including osteogenic materials, received within their barrel portions for delivery, and syringe-based methods for delivering medical substances, such as osteogenic materials, into the interbody space between two adjacent vertebra. Such methods include minimally-invasive methods which may involve the use of cannulated surgical access elements such as laproscopes or introducer sleeves. Embodiments of the present invention also include surgical apparatuses, kits and systems that include syringe devices as described above potentially in combination with such laproscopes, sleeves, and/or other instruments useful in the related surgical procedures, as well as subcomponents of syringe devices as described above and elsewhere herein, including novel syringe barrel constructs, novel control sheath constructs, novel syringe plunger constructs, novel control rod constructs, and novel methods of their use, particularly but not exclusively where such apparatuses, kits, systems, subcomponents and methods are adapted and suitable for use in minimally-invasive spinal interbody procedures, such as fusion procedures.

Additional embodiments as well as features and advantages of the invention will be apparent to those of ordinary skill in the art from the further descriptions herein.

BRIEF DESCRIPTION OF THE FIGURES

Various embodiments of the present invention will be discussed with reference to the appended drawings. These drawings depict only illustrative embodiments of the invention and are not to be considered limiting of its scope.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations and further modifications in the described embodiments, and such further applications of the principles of the invention as illustrated therein being contemplated as would normally occur to one skilled in the art to which the invention relates.

As disclosed above, the present invention provides syringe based methods, syringe devices, systems and subcomponents that are useful for delivering medical substances to patients. In particular aspects of the invention, such methods, devices systems and subcomponents are configured to be useful for delivering bone growth materials such as osteogenic formulations to an interbody space between adjacent vertebra of a patient, e.g. in the conduct of an interbody spinal fusion procedure.

Figure 1:
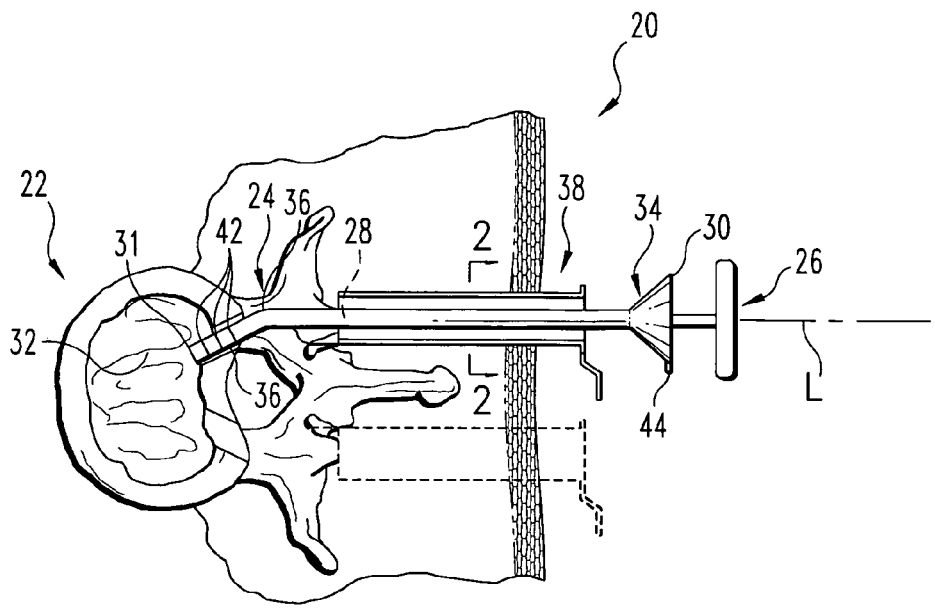
FIG. 1 is a perspective view of an illustrative embodiment of a syringe device according to the present invention in use to deliver osteogenic material to an interbody disc space.
Figure 2:
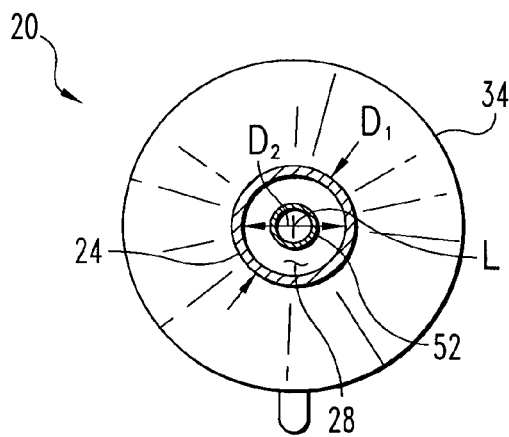
FIG. 2 is a cross-sectional view of the syringe device of FIG. 1 along section line 2-2 and viewed in the direction of the arrows.
Figure 3:
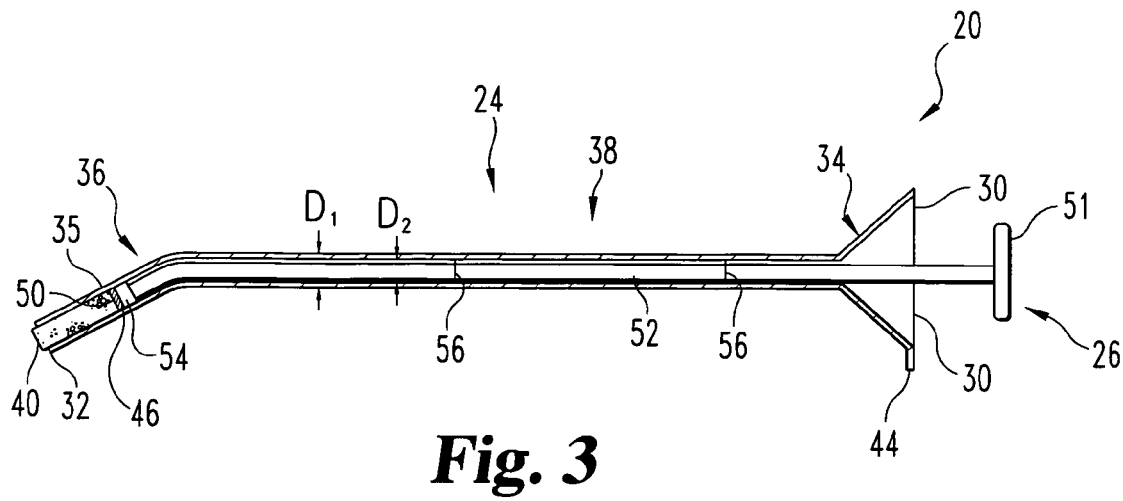
FIG. 3 is a partial cross-sectional view of the syringe device of FIG. 1.

Referring now generally to FIGS. 1-3, depicted is a syringe device 20 which useful for delivering a medical material, and that is especially advantageous in delivering a plug of porous material that is susceptible to undesired compression that would expel a liquid formulation from the plug. In particular, provided in FIG. 1 is a depiction of the illustrated syringe device in use to deliver an osteogenic material to a location in the spine 22 of a patient, specifically into the interbody space 32 between a first vertebral body and a second vertebral body. The depicted procedure represents a type of minimally-invasive procedure, in which access to the interbody space 32 is provided using a posterior approach with the introduction of an introducer sleeve 500. It will be understood that other types of minimally-invasive accesses through small incisions (e.g. about 30 mm or less) can also be used in the invention, including for instance laproscopic anterior surgical approaches and mini-open surgical approaches.

Syringe device 20 includes a barrel portion 24 and a plunger apparatus 26 configured to travel within the barrel portion 24. Barrel portion 24 has an internal lumen or chamber 28 extending therein, a proximal end 30, and a distal end 31. Proximal end 30 and distal end 31 are open ends configured for receipt and delivery, respectively, of the material to be delivered by the syringe device 20. The barrel portion 24 further includes a broadened or funnel portion 34 at its proximal end 30, a distal dispensing segment 35 having a curve 36 opposite the funnel portion 34, and a central portion 38 connecting the funnel portion 34 and the dispensing segment 35. As illustrated, funnel portion 34 and central portion 38 generally extend along a longitudinal axis L. Additionally, funnel portion 34, central portion 38, and distal dispensing segment 35 include generally right-circular cross-sectional dimensions. However, it should be appreciated that the other cross-sectional shapes may be used within the scope of the present invention. Additionally, it is contemplated that funnel portion 34 can include a wider or narrower funnel-shaped configuration as would generally occur to one skilled in the art to perform the load-assist functions of funnel portion 34. Further, it will be understood that in some embodiments of the present invention, the funnel portion 34 can be absent.

As illustrated, dispensing segment 35 includes a curved or arcual configuration. In the illustrated embodiment, the curved portion 36 of the distal dispensing segment 35 terminates short of the distal end 32, and is followed by a relatively short, straight segment. However, it should be appreciated that the curved configuration 36 of dispensing portion 35 can terminate at distal end 32 in other inventive embodiments. Additionally, it is contemplated that the degree of curvature of curve 36 could vary from the illustrated degree of curvature, while maintaining the functionality of dispensing segment 35 in delivering material in a direction other than that of the longitudinal axis L. In certain embodiments, the curve or deflection will position the axis of the distal delivery opening at an angle from about 1° to about 90° relative to longitudinal axis L. In certain preferred embodiments, such angle will be between about 3° and about 45°. Still further, in one alternative embodiment, the curve 36 of the dispensing segment 35 is absent and the distal dispensing segment 35 generally extends along longitudinal axis L. Moreover, it will be understood that dispensing segment 35 could include still other configurations that are effective in delivering implantable material to a desired tissue site.

Central portion 38 is generally cylindrical, at an angle extending along longitudinal axis L, with a right-circular cross-sectional shape. Alternatively, central portion 38 could include a curved configuration similar to that of dispensing portion 36, extending transverse to longitudinal axis L. Central portion 38 in the illustrated embodiment provides a continuous connection between funnel portion 34 and the distal dispensing segment, with all portions being a single manufactured piece. However, it will be understood that differing segments of the syringe barrel 24 can be made from differing, connected pieces. For instance, central portion 38 can be a separate piece connected to funnel portion 34 and the distal dispensing segment 35 including curved portion 36. It is also contemplated that the various components of syringe device 20 can be composed of a plastic material, or alternatively another biocompatible material such as metal that enables the syringe device 20 to perform the functions stated herein.

Referring now particularly to FIG. 2, provided is a cross-sectional view of the syringe device 20 taken along section line 2-2 and viewed in the direction of the arrows. As illustrated, the outer cross-section of the syringe barrel 24 is generally right circular in shape about longitudinal axis L (indicated by cross-hairs in FIG. 2) and provides an outer diameter D1. Further, the inner cross-section of barrel 24 is also right circular in shape about longitudinal axis L and provides an inner diameter D2. It will be understood, however, that the outer and/or inner cross-sectional shapes or dimensions of the syringe barrel can vary from those shown, and could vary along the length of the barrel. These and other modifications to the barrel will be apparent to the skilled artisan from the descriptions herein.

FIG. 3 provides a partial cross-sectional view of the syringe device 20 taken along its longitudinal axis and illustrating plunger apparatus 26 within the internal chamber or lumen 28 of the syringe barrel 24. The syringe device 20 as illustrated in FIG. 3 is shown at a stage wherein it is delivering a compressible medical implant material such as a porous compressible plug 40. In certain embodiments of the invention, plug 40 includes a liquid carrier comprising an osteogenic substance such as a bone morphogenetic protein (BMP) imbibed within pores of the plug 40. However, it should be appreciated that the syringe device 20 can be used move and dispense other materials as well.

Figure 2A:
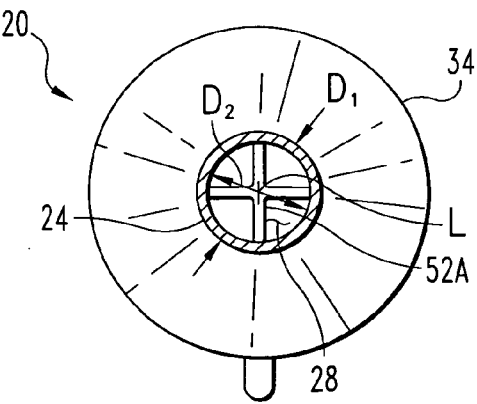
FIG. 2A is a cross-sectional view depicting an alternate plunger arm of a syringe device of the invention.

The plunger apparatus 26 includes a material contacting distal tip 50, a proximal handle portion 51, a plunger head 54, and a plunger arm 52 connecting the tip 50 and the handle 54. As depicted in FIG. 2, plunger arm 52 can have a generally right circular cross section, similar to but smaller than that of syringe barrel portion 24. Additionally, such a plunger arm 52 can optionally be equipped with a series of guide fins 56 (shown in FIG. 3). In one embodiment, the guide fins 56 are positioned circumferentially around the body 52 of the plunger apparatus 26, extending radially outward from the body 52 to contact the inner surface of the barrel 24. The guides 56 facilitate the smooth, centered travel of the plunger apparatus through the internal lumen 28 of the syringe barrel portion 24. In the illustrated embodiment, there are two discrete segments of plunger arm 52 that include guide fins 56; however, it is contemplated that in other embodiments the guide fin segments could number more or less than two along the plunger arm 52 or the fins could extend the whole length of plunger arm 52. Furthermore, with specific reference to FIG. 2A, the plunger arm in alternative embodiments can take on other cross-sections, including for example a generally cross-shaped ("+") section having four radially-extending, barrel-contacting arms spaced at 90° from one another, as shown for plunger arm 52A.

Continuing with reference to FIG. 3, plunger head 54 is sized to allow movement of the plunger head 54 through internal lumen 28 so as to effectively advance a material contained within lumen 28 toward the distal open end of the syringe barrel portion 24. Plunger head 54 can be made from a relatively compressible material such as a rubber or elastomeric material, and can include a non-constrained cross-sectional diameter approximately equal to or slightly greater than the internal diameter D2 of the syringe barrel portion 24. As illustrated in FIG. 3, the plunger arm 52 is sufficiently flexible to adopt a curved configuration to travel along the curved portion 36 of the distal dispensing segment 35 of syringe barrel portion 24 and move implant material plug 40 therethrough.

Syringe device 20 can also include elements or markings at its proximal regions that will remain external or nearly external of the patient and will be directly visible to the eye of the user, which elements or markings or other visible indicia are correlated to and thereby indicate the position or orientation of more distal elements of device 20. In addition or alternatively, syringe device 20 can include one or a plurality of radiopaque markers or other imagable (e.g., MRI, ultrasonic, etc.) markers on the more distal regions of the barrel 24 and/or the plunger apparatus 26 that will enter sufficiently into the patient to be non-visible to the naked eye of the user. Specifically, in the illustrated embodiment 20, imagable marker bands 42 are provided at the distal segment of barrel 24, including at least one which marks the distal tip 31 of the barrel 24. Also, imagable markers 42 can provide a scale for reference by the user if desired. Plunger head 54 can also have an imagable marker 46 denoting its distal tip to enable tracking of the plunger head 54 through the barrel 24 during use. As to proximally-positioned visible indicia, device 20 includes a tab 44 adjacent to its proximal end which is aligned with the direction of deflection of distal segment 35 relative to the longitudinal axis L. It will be understood that other visible elements, markings or shapes could also be used to provide such correlative visible indicia between proximal and distal structures of device 20.

Figure 4:
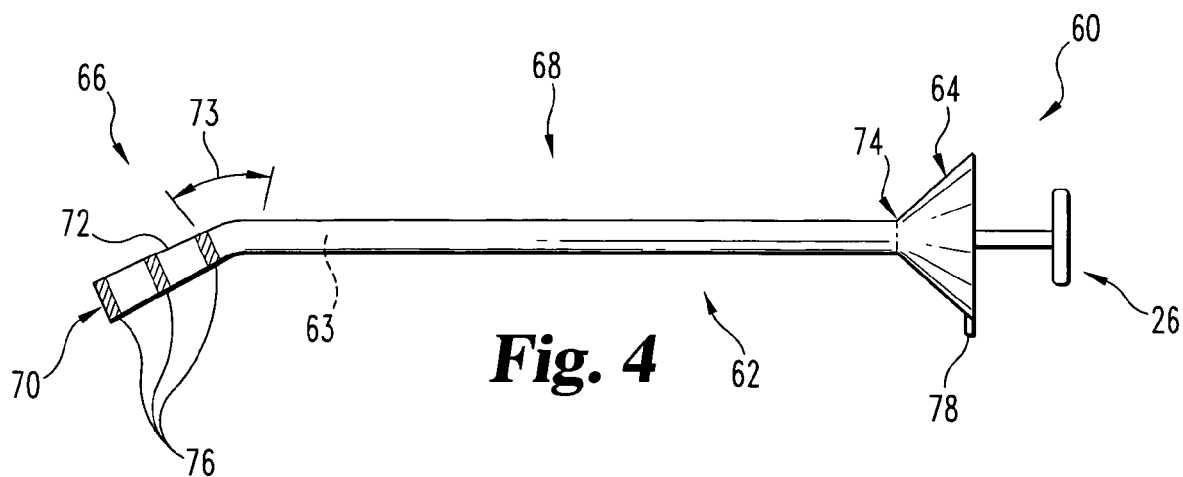
FIG. 4 is a perspective view of another illustrative embodiment of a syringe device according to the present invention.

FIG. 4 illustrates a syringe device 60 according to another embodiment of the present invention. The device 60 includes plunger apparatus 26 and a barrel portion 62 having an internal lumen 63. The barrel portion 62 includes a funnel portion 64, a dispensing portion 66 opposite the funnel portion 64, and a central portion 68 connecting the funnel portion 64 and the dispensing portion 66. The barrel 62 also includes a distal open end 70. Syringe device 60 preferably includes a tapered region 72 of increasing inner diameter in a direction extending toward distal open end 70. Tapered region 72 can assist in preventing an implant material (e.g., plug 40) from experiencing resistance to travel within lumen 63 and thus in the case of compressible implant material, can decrease or prevent any undesired compression during delivery. In the illustrated embodiment, tapered region 72 is located in the distal dispensing segment 66, with an increasing lumenal dimension beginning just at or after curved portion 73 and continuing to taper outwardly to distal open end 70. However, it should be appreciated that other beneficial tapered regions could be incorporated into lumen 63 of syringe barrel 62. For example, in one embodiment, the tapered region could begin at funnel connection point 74 and provide a continuous increase in the inner diameter or lumenal cross-section along barrel 62, terminating at distal open end 70. In alternative embodiments, syringe barrel could include one or more steps of increasing inner diameter or lumenal cross-section along its length, with the increases extending in a direction toward distal open end 70. Further, it will be understood that the outer diameter or configuration of barrel 24 need not change when the inner diameter changes, such that a consistent outer diameter can occur along barrel 24 while the internal lumen varies. These and other variations can be practiced within the invention.

In addition, in certain embodiments of the invention, the diameter or cross-sectional profile of internal lumen 63 will remain substantially constant or will increase from a point corresponding to the trailing end of a loaded medical material (e.g. funnel connection point 74) to the distal open end 70. In this fashion, the internal lumen 63 can be constructed so as to be free of constriction points or transversely-extending walls that would impede the advance of graft materials out of distal delivery opening 70, and that would potentially lead to the undesired compression of a compressible graft plug material having pores loaded with a liquid pharmaceutical formulation. Similar considerations apply to syringe device 20 depicted in FIGS. 1-3. In this regard, it will also be understood that the syringe devices depicted in these and other Figures herein are preferably constructed and used as needleless syringe devices, and thus will free from any needle mounted to the distal open end of the syringe barrel.

Generally referring to FIGS. 1-4, an illustrative operation of syringe devices 20 and 60 will be described. Syringe device 20,60 is loaded with a medical material at funnel portion 34,64. Plunger apparatus 26 is inserted into the internal lumen 28,63 of the barrel 24,62 of the syringe device 20,60. In the illustrated embodiment, the plunger apparatus 26 enters the barrel 24,62 at its proximal end with material contacting tip 50 contacting the material to be dispensed or delivered, such a porous plug 40. However, it should be appreciated that the plunger apparatus 26 could enter and/or operate from a different position along barrel 24,62 for example, using a modified barrel with a side-entry port for the plunger apparatus 26. The loaded syringe device 20,60 is thereafter manipulated to position its distal delivery opening at a desired location in a patient's body for instance in a spinal interbody space. However, it should be appreciated that the syringe device 20,60 can be loaded with a material after manipulation to the desired position including an original material loading and/or a re-loading.

After positioning of syringe device 20,60, an actuating force is applied to the handle 51 of plunger apparatus 26. As a result, the loaded material, such as plug 40, is moved within internal lumen 28,63 of barrel 24,62 toward its distal end by plunger apparatus 26. The guides 56 disposed about the arm 52 of the plunger apparatus 26 guide the plunger apparatus 26 down a longitudinal centerline of the internal lumen 28, 63 of the barrel 24. The implant material plug 40 is thereby moved through internal lumen 28,63 of barrel 24 62 and dispensed at the desired location. At least a portion of the plunger arm 52 adopts a curved configuration to travel within the curve 36,73 of dispensing segment 35,6 to move the material therethrough. In one application, it is contemplated that plug 40 contains a liquid formulation comprising an osteogenic protein such as a BMP and is dispensed without substantial compression during travel through the barrel lumen 28,63 into an intervertebral disc space to promote bone growth and fusion between adjacent vertebral bodies.

Specifically regarding the syringe device 60 of FIG. 4, tapered region 72 facilitates movement of the material to be dispensed along the curved dispensing portion 66 without substantial loss of the material or fluid contained in a compressible carrier, such as leakage from plug 40 as an example. Tapered region 72 preferably includes a sufficiently increasing cross-sectional dimension so that the material is facilitated in negotiating the curved configuration of the dispensing portion 66 without excessive pressure applied on the material.

In alternative embodiments of the present invention, modified mechanisms for advancing material through syringe barrels can be employed. For example, the plungers may be threaded so that they advance when rotated to cooperate with corresponding threads of the syringe barrel. In other alternative embodiments, trigger-actuated plungers can be used, or the plunger can be absent and a pneumatic, hydraulic or another such motive force can be utilized to move and dispense the medical material through syringe barrels of the inventive devices.

With reference now to FIGS. 5-22, shown are a number of additional embodiments of the present invention, in which a syringe device is combined with at least one additional element in a manner wherein the syringe and additional element cooperate to enable the selective regulation of the configuration of the syringe barrel, for example to introduce and remove or decrease a deflection or arcual bend in the distal region of the syringe barrel. This cooperation may be used, for example, during surgical procedures for delivering an implant material or other medical substances to an interbody space adjacent first and second vertebra. Illustratively, such procedures may involve positioning the distal region of the syringe barrel within the interbody space in a first configuration, and thereafter causing the distal region to adopt a second configuration. This may facilitate the delivery of the medical substance to a particular location or across a broader region of the interbody space. In certain embodiments, the distal region of the syringe barrel is inserted into the disc space in a relatively straight configuration and is thereafter caused to adopt a deflected or curved configuration that positions the tip of the syringe barrel and its delivery opening in a new location.

Figure 5:
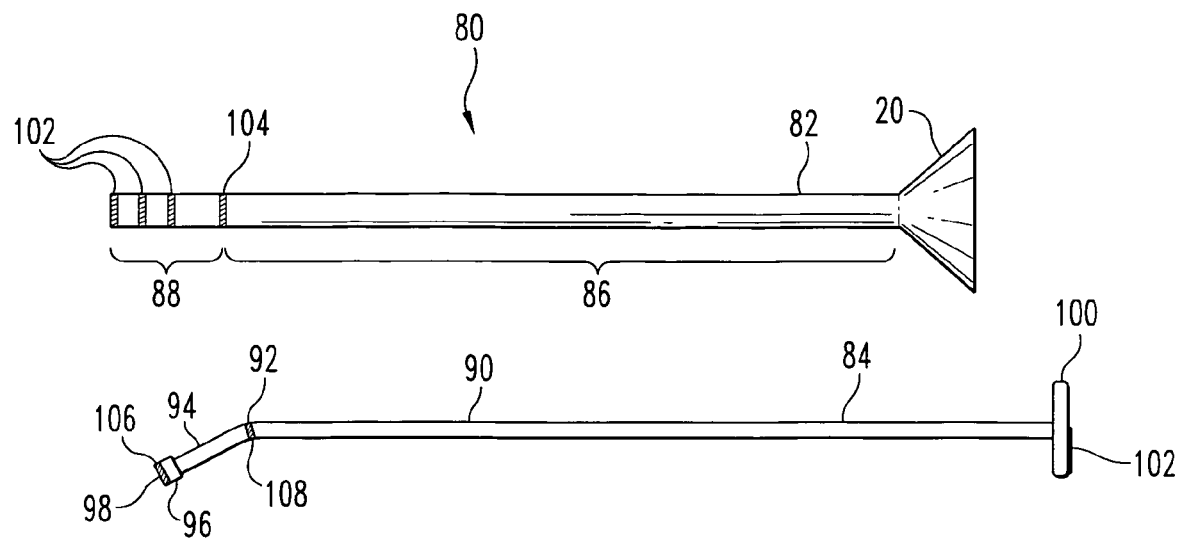
FIG. 5 provides a perspective view of a syringe device of the invention wherein a plunger arm and barrel are cooperable to deflect the distal region of the barrel.
Figure 6:
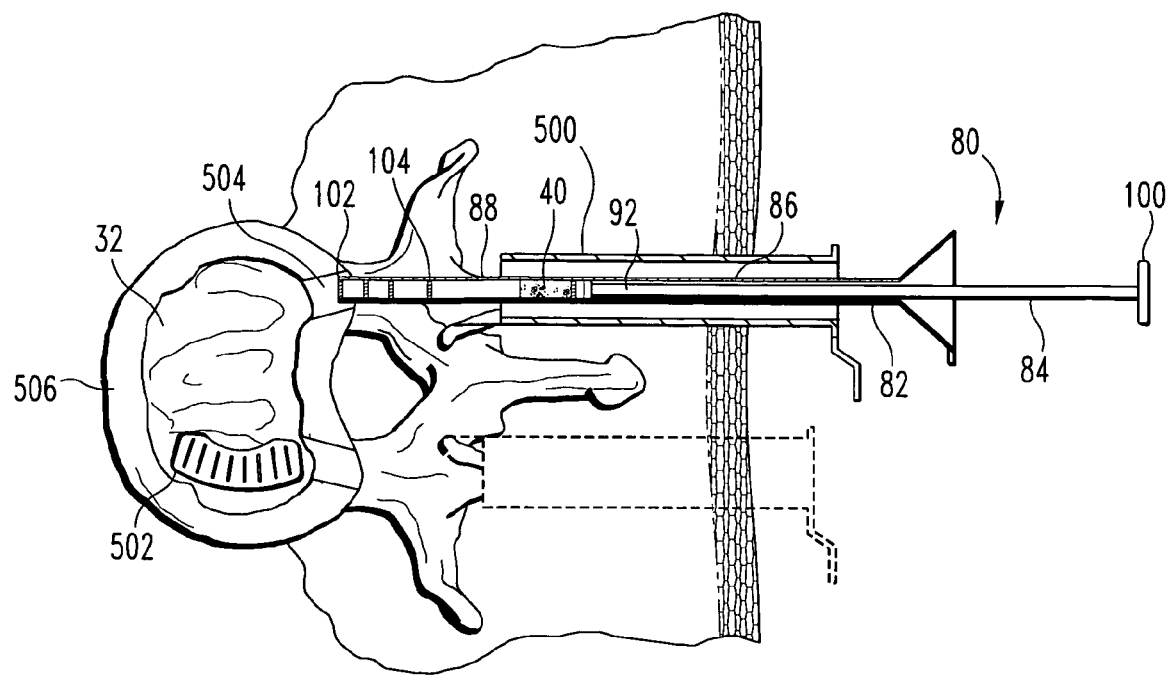
FIGS. 6 and 7 provide partial cross-sectional views depicting the syringe device of FIG. 5 in use to deliver medical material to an interbody disc space.
Figure 7:
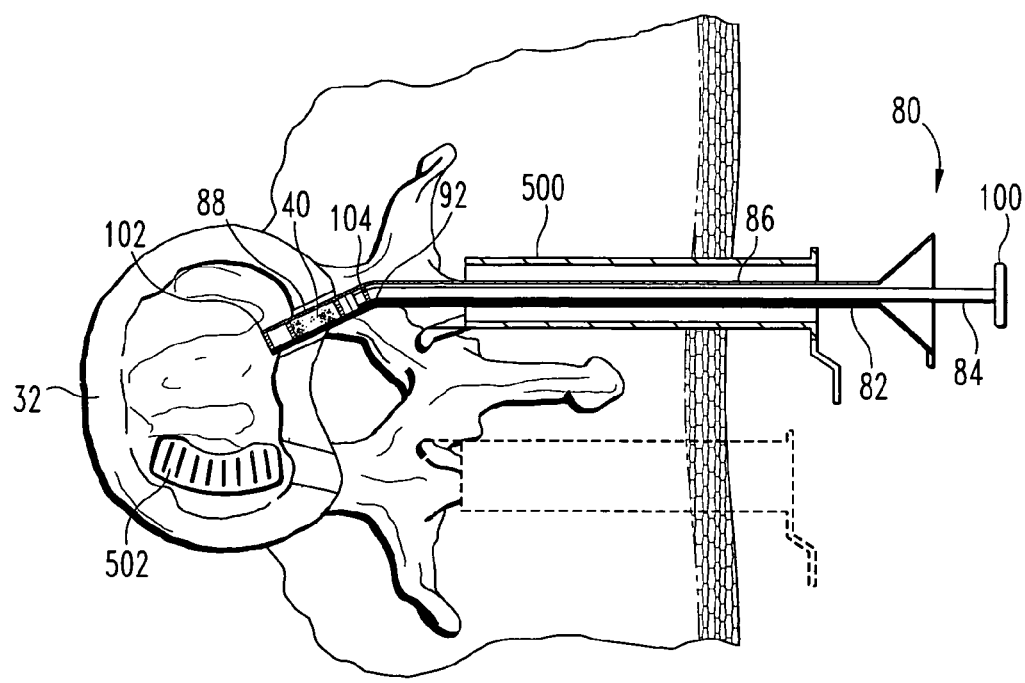

With reference now particularly to FIGS. 5-7, shown is one embodiment of a delivery syringe device of the present invention wherein cooperation between a plunger arm and a syringe barrel achieves a deflection or curve in the distal region of the syringe barrel. The syringe device 80 illustrated includes a syringe barrel portion 82 and a plunger apparatus 84. Syringe barrel portion 82 includes a first segment 86 and second segment 88, wherein the second segment 88 is more flexible than the first segment 86. Second segment 88 occurs in a distal region of the syringe barrel portion 82, and in accordance with the invention will be deflectable in use. A transition occurs between segments 86 and 88, and that transition is marked with an imagable marker 104 in certain embodiments of the invention. In this regard, the transition can represent any suitable change of material properties between segments 86 and 88, including for example a butt-weld of differing materials, a transition of the thickness or properties of a single or integral piece of material, a reduction in the number of layers of a similar material, etc. Any suitable means or mechanism by which segment 86 and 88 have differing flexibility as indicated can be used within the scope of the present invention.

Figure 5A:
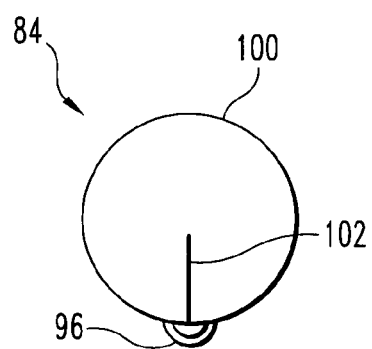
FIG. 5A provides a right end view of the plunger apparatus depicted in FIG. 5.

Turning now to the plunger apparatus 84, it generally includes a plunger arm 90 having a bend 92 therein. In certain embodiments as depicted, bend 92 can be followed in the distal direction by a generally straight segment 94, with a plunger head 96 positioned at the distal end thereof. Plunger head 96 provides a leading end surface 98 for contact with a graft material or other medical substance to be delivered. Plunger apparatus 84 also includes a handle portion 100. Referring particularly to FIG. 5A, handle portion 100 in an advantageous embodiment includes a visible marking 102 which corresponds to the direction of the bend 92 in the plunger arm 90, thus providing a visible indication to an user as to which direction the leading end surface 98 of the plunger apparatus 84 will be deflected when the distal regions of the plunger arm 90 are not otherwise visible to the user, for example when they are deployed within tissues of the patient. In other advantageous features, syringe barrel portion 82 can include imagable distal tip markers 102, and a funnel portion as previously described. As well, plunger head 96 of plunger apparatus 84 can include an imagable marker 106 such as a band, so that movement of the plunger head 96 within the barrel portion 82 can be detected under an imaging system in operation during the surgical procedure. Plunger arm 90 can also include an imagable marker 108 located at the transition of its relatively straight segment with the deflected segment 94. In this manner, referencing markers 108 and 104, a user can obtain information as to at what point deflection of the segment 88 will occur. Alternatively or in addition, visible markers can be provided on proximal regions of barrel portion and/or plunger arm 90 that will remain external of the patient and thereby directly visible to the user. These visible markers can be at positions whereby they align with other visible markers or component features when more distal, non-visible component features reach a correlated state of alignment. As one example, the plunger arm 90 can include a visible proximal marker that aligns longitudinally with the proximal-most end surface of syringe barrel portion 82 when leading end surface 98 of plunger head 96 reaches the transition between relatively rigid segment 86 and more flexible segment 88. Such correlative proximal visible markings can be used on the other syringe devices disclosed herein as well to indicate the position, alignment or orientation of more distal structures.

The materials and/or construction of the plunger arm 90 and the segments 86 and 88 are selected such that the relatively stiff or rigid segment 86 of the barrel portion 82 has the capacity to deflect the bend 92 of the plunger arm 90 into a straight condition for travel through segment 86. However, when bend 92 of plunger arm 90 is advanced to and beyond the transition between segments 86 and 88 of syringe barrel portion 82, advantageously marked by marker 104, the plunger arm 90 and in particular its bend portion 92 has the capacity to deflect the relatively more flexible segment 88 of syringe barrel portion 82 to a new configuration. In this manner, the distal delivery of opening syringe barrel 82 is repositioned relative to its original position when segment 88 existed in a straight or at least less deflected or curved condition. Accordingly, in certain embodiments of the invention, segment 86 will be stiffer than plunger rod 90, which in turn will be stiffer than segment 88 of syringe barrel portion 82.

Referring now specifically to FIGS. 6 and 7, in use, syringe device 80 can be deployed in a minimally invasive surgical procedure to deliver a medical material to an interbody space 32 between first and second adjacent vertebra. Illustratively, such delivery can be a component of an interbody spinal fusion procedure in which one or more load-bearing spinal implants, e.g. implant 502, are delivered into the interbody space 32. Such loadbearing implants may be delivered through the same access through the syringe device is manipulated, and/or through another access to the same interbody disc space, for example through an opposite posterior access (see second introducer sleeve shown in phantom).

With reference to FIG. 6, illustrated is a point in a minimally invasive spinal interbody fusion procedure wherein access has been gained via an introducer tube or sleeve 500. Similar access has previously been gained to the opposed side of interbody space 32 and load-bearing implant 502 introduced. At the illustrated point in the procedure, syringe device 80 is positioned in its overall straight configuration for passage through introducer sleeve 500, through opening 504 existing or created in the annulus fibrosus, and into interbody space 32. Thus, plunger apparatus 84 is in a relatively withdrawn position within syringe barrel portion 82 with its deflection point 92 residing within relatively stiff segment 86 of barrel portion 82 thereby forced to a straight or relatively straight configuration. Graft material 40 lies in advance of leading end surface 98 of plunger head 96, and relatively flexible segment 88 is passed through opening 504 and into interbody space 32. Referring again to FIGS. 6 and 7 together, plunger apparatus 84 is forced into syringe barrel portion 82 using handle 100 to translate plunger head 96 distally within syringe barrel portion 82 thus also advancing graft material 40. Upon and after plunger 96 enters relatively more flexible segment 88 of syringe barrel portion 82, the distal tip and delivery opening of syringe barrel portion 82 begin to deflect to a new configuration and position, for example as generally shown in FIG. 7. Continued advancement of plunger apparatus 84 ultimately delivers graft material 40 out of the distal delivery opening of syringe barrel portion 82. In the illustrated embodiment, the distal region of syringe barrel portion 82 is deflected generally toward the center of the interbody space 32 from a more lateral position thereby enabling a more central delivery of the graft material 40. It will also be understood that amounts of graft material 40, which may be originally loaded material or re-loaded material, can be delivered with the syringe barrel in straight or other configurations as compared to that shown in FIG. 7. In certain embodiments, the plunger apparatus 84 can be withdrawn proximally within syringe barrel portion 82 until relatively stiff segment 86 of barrel portion 82 again straightens plunger rod 84 and distal segment 88 resiliently returns to a straightened configuration, whereupon handle 100 can be rotated, desirably with reference to visible deflection marker 102 on the end of handle 100, to provide a new direction of deflection. Plunger apparatus 84 can thereafter re-advanced distally within barrel portion 82 to reposition the distal delivery opening of barrel portion 82 for delivery of amounts of graft material in other locations. Of course, it will be understood that plunger apparatus 84 can also be rotated with plunger head 96 positioned within flexible segment 88, to cause the distal region of syringe barrel portion 82 to move from one deflected position to another or a plurality of other positions for delivery of additional amounts of graft material 40. As well, the entire syringe device 80 could be rotated while in its straight configuration, and plunger apparatus 84 then re-advanced to reposition the distal delivery opening.

In certain spinal fusion procedures of the invention, a second loadbearing spinal implant similar to that shown as 502 will be introduced on the other side of interbody space 32. This may be performed after delivery of amounts of graft material 40 centrally within interbody space. As well, syringe device 80 can be used to deliver additional amounts graft material in and around inserted implant 502 and its opposite counterpart implant, to further aid in the fusion process.

Figure 8:
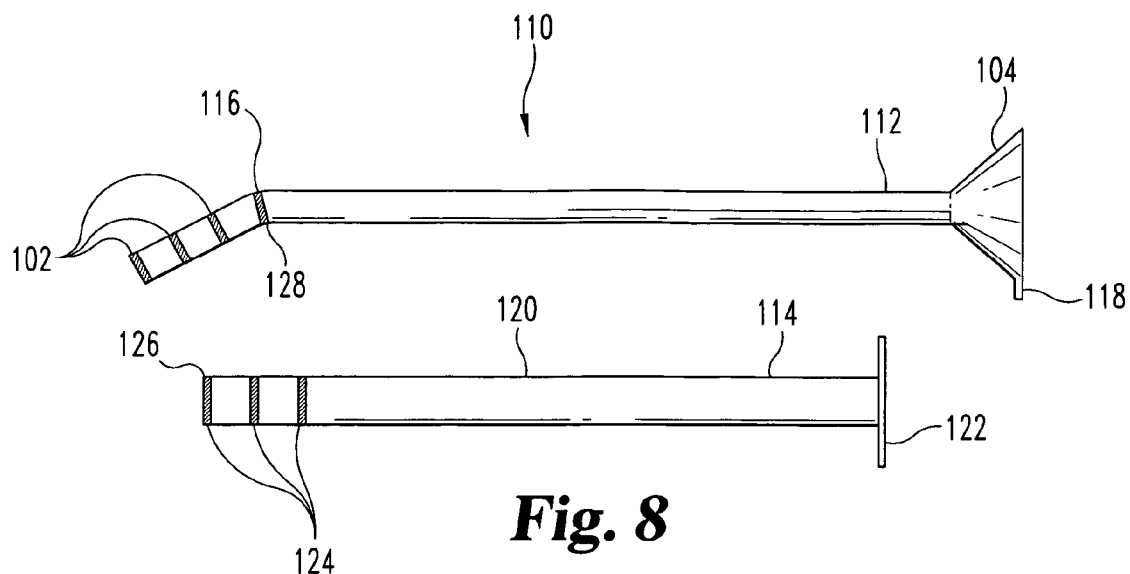
FIG. 8 depicts a syringe device having a barrel and external sheath cooperable to selectively constrain and unconstrain a curved portion of the syringe barrel.
Figure 9:
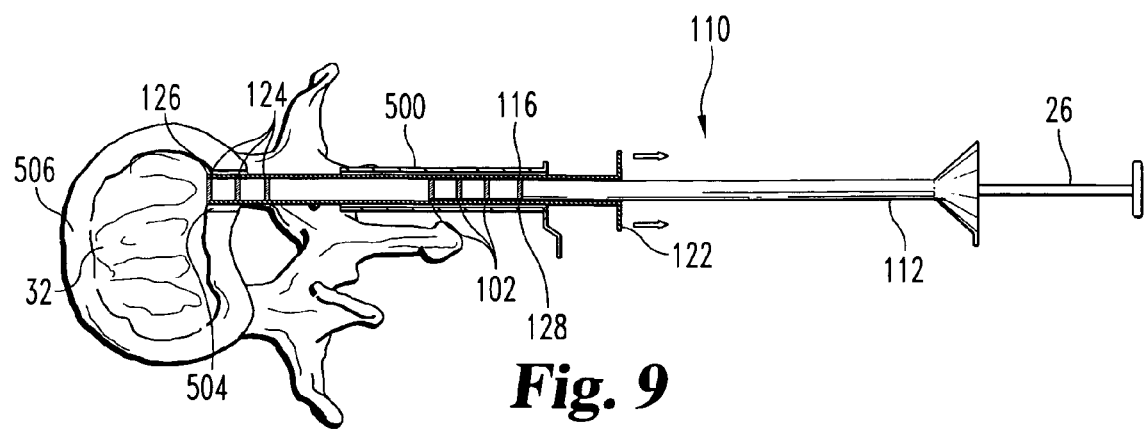
FIGS. 9 and 10 depict the device of FIG. 8 in use to deliver a medical material to an interbody disc space through a cannulated, minimally invasive posterior access.
Figure 10:
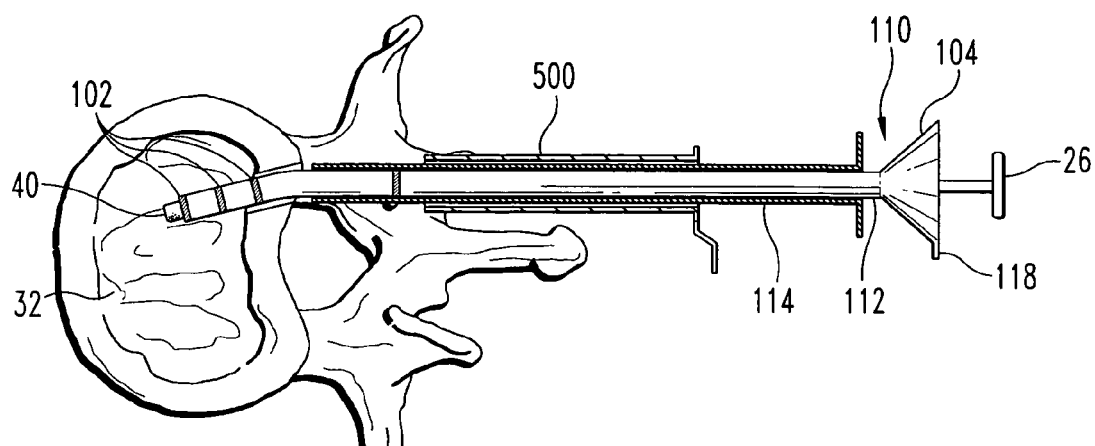

With reference now to FIGS. 8-10, shown is an alternative embodiment of the present invention. In particular, a syringe device 110 includes a syringe barrel portion 112 and an outer sheath 114 receivable over and translatable or slidable along barrel portion 112. In this illustrated embodiment, the sheath 114 is relatively more rigid than the syringe barrel portion 112 and thereby can cooperate with barrel portion 112 to selectively straighten or allow deflection of a distal segment of barrel portion 112.

Specifically, syringe barrel portion 112 includes a bend 116 in a distal region thereof. Barrel portion 112 can also include a tab 118 or other visible marking on its funnel portion 104, corresponding to the direction of the bend 116 to provide visible indicia to a user generally as discussed above. Sheath 114 includes a sheath body portion 120 relatively more stiff than syringe barrel 112 and in particular stiffer at least than the region of barrel portion 112 at and around bend 116. In this regard, it will be understood that so long as the properties of syringe barrel 112 at bend 116 are such that sheath 114 has appropriate portions that can force bend 116 to a straightened configuration, the objectives of the controllable syringe barrel embodiments of the invention will be met. Thus, for example, the entire length of syringe barrel portion 112 can be constructed to be more flexible than the body 120 of sheath 114. Alternatively, one or both of the segments of syringe barrel 112 flanking bend region 116 may be made of a material or of a construction that would not be deflectable by sheath body 120, but bend region 116 could nonetheless include a material or construction capable of deflection by sheath body 120, or at least the portions of sheath body 120 that will be positioned to cooperate with bend region 116. It will be understood these and other adaptations may be applied to components of syringe device 110, as well as to components of the other embodiments disclosed herein wherein cooperation between a syringe barrel portion and a secondary element is used to achieve control of a distal region of the syringe barrel.

With continued referenced to FIGS. 8-10, sheath 114 can include a collar 122 as well as imagable distal position markings 124 adjacent to its distal end 126. Distal region imagable markings 124 of sheath 114 can for example can be used in conjunction with an external imaging system to monitor the position of the distal region of the sheath 114, including in relation to the bend 116 of barrel portion 112, which itself can be marked with an imagable marker 128. Marker 128 can be the same as markers 102 and 124, or may be of a differing nature, such as wider or narrower, having a differing pattern or marking, etc. Markings upon the various components which differ one another in these and other depicted embodiments of the invention will be advantageous in that they will allow the user to more readily discern and differentiate the structures observed using the imaging system in operation.

FIGS. 9 and 10 illustrate the use of syringe device 110 at different stages during a minimally invasive surgical procedure accessing interbody space 32. In particular, shown in FIG. 9 is syringe device 110 in its relatively straight configuration for advancement into the interbody space 32. Thus, syringe barrel portion 112 is received within sheath 114 having its bend 116 as well regions distal thereof received within the body 120 of sheath 114. Sheath 114 has its distal end 126 advanced into the opening 504 in disc annulus 506. Referring now to FIG. 10, syringe barrel portion 112 is advanced into sheath until bend portion 116 exits the distal end 126 of sheath 114. Bend portion 116 thereupon returns to its relaxed, bent or deflected configuration thus repositioning the distal delivery opening of syringe barrel portion 112. The exit of bend portion 116 from sheath 114 can be monitored for example using imagable bend marker 128 on syringe barrel portion 112 in combination with distal region markers 124 on sheath 114. Thereafter, a plunger apparatus 26 (or one such as 84 depicted in FIG. 5 that can be straightened by sheath 114) can be forced distally through syringe barrel 112 to deliver a graft material 40 from the distal delivery opening of syringe barrel portion 112. The direction of travel of the distal delivery opening of syringe barrel portion 112 caused by bend portion 116 can be monitored visually by a user by reference to tab 118 or another similar visible indicia. As with the embodiment depicted in FIGS. 5-7, the distal delivery opening of syringe barrel portion 112 can be repositioned by rotation of the syringe barrel portion 112, either with the bend portion 116 retracted into sheath 114 (and thus constrained to a straight condition) or with bend portion 116 distal of end 126 of sheath 114 thus positioning the delivery opening to a number of deflected positions.

Figure 11:
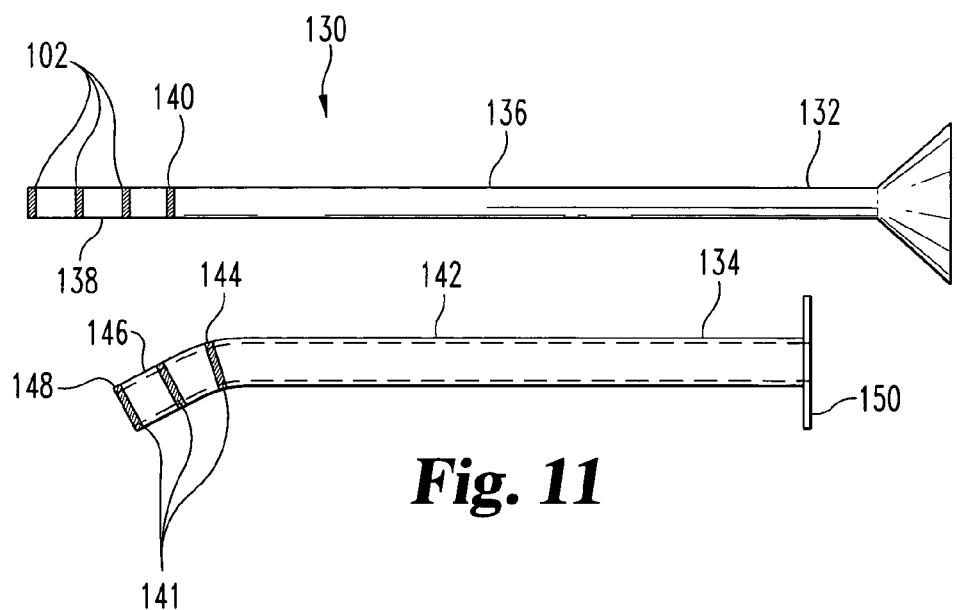
FIG. 11 illustrates a syringe device having a barrel and external sheath cooperable to impart a curve to an otherwise straight distal segment of the barrel.
Figure 11A:
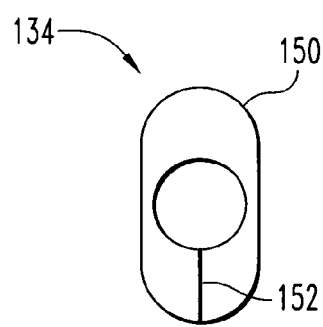
FIG. 11A provides a right end view of the sheath component depicted in FIG. 11.
Figure 12:
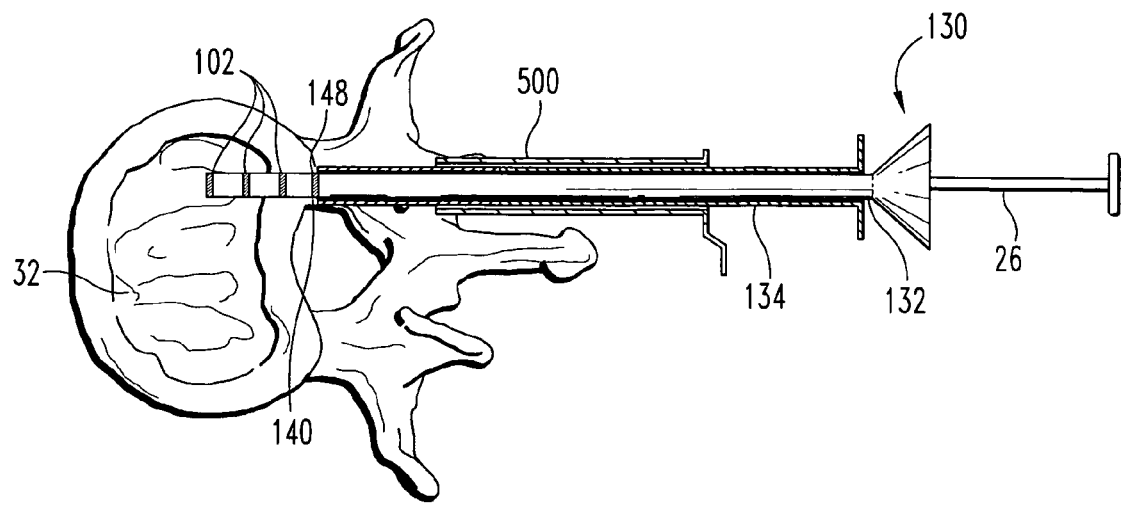
FIGS. 12 and 13 depict the device of FIG. 11 in use during a minimally invasive spinal fusion procedure with a cannulated posterior approach.
Figure 13:
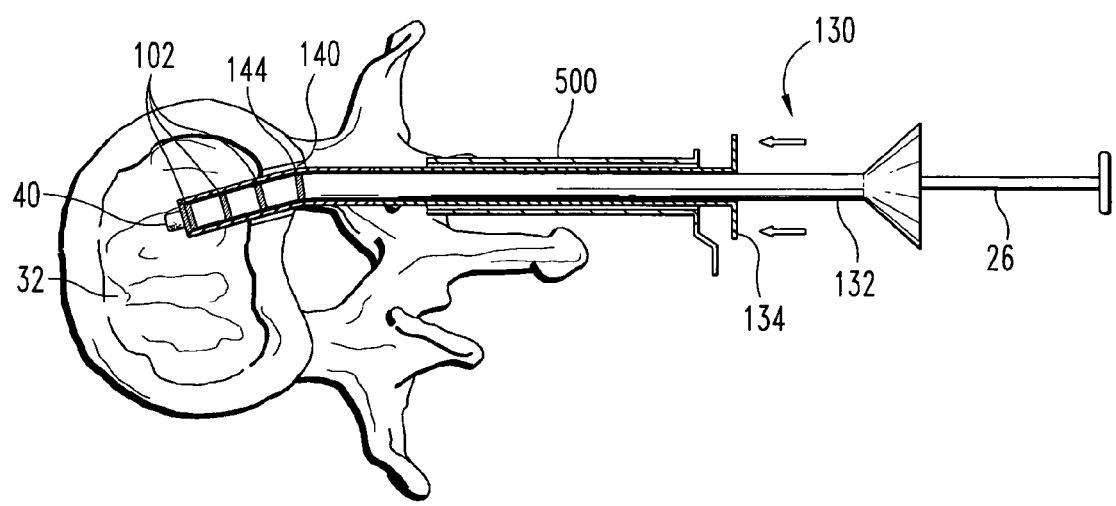

With reference now to FIGS. 11-13, shown is another syringe device 130 of the invention in which a syringe barrel portion is cooperable with a sheath to control the tip and delivery opening of the syringe barrel portion. In particular, syringe device 130 includes syringe barrel portion 132 and sheath 134. Syringe barrel portion 132 includes an elongate body having a relatively stiff portion 136, a relatively flexible portion 138, and a transition therebetween, for example marked by imagable marker 140 in the illustrated device. Sheath 134 includes an elongate body having a relatively straight portion 142, a bend 144, and a relatively straight segment 146 distal of the bend 114 and terminating in distal end 148. Sheath 134 includes a collar 150. Referring specifically here to FIG. 11A, collar 150 can include a visible marking 152 corresponding to the direction of bend 144 in the sheath 134. Sheath 134 is constructed such that bend 144 is constrainable to a relatively straight configuration by stiff segment 136 of syringe barrel portion 132. On the other hand, sheath 134 and flexible segment 138 of syringe barrel portion 132 are constructed such that bend portion 144 is capable of deflecting distal flexible segment 138 of syringe barrel portion 132. In this manner, syringe barrel portion 132 and sheath 134 are cooperable to deflect the distal region 138 when bend 144 is received thereupon, and wherein bend 144 is constrained to a straight condition when received upon proximal stiffer region 136 of syringe barrel portion 132.

Referencing FIGS. 12 and 13, in use, syringe device 130 can be advanced through a cannulated or otherwise minimally invasive access to an interbody space 32 while in a straight configuration so as to position the distal delivery opening of syringe barrel portion 132 within the interbody space. This positioning can be tracked using distal markings 102. This straight configuration includes sheath 134 withdrawn relatively proximally onto to syringe barrel portion 134 (see generally FIG. 12). After this, sheath 134 can be advanced distally along syringe barrel portion 132 until bend portion 144 exits stiff segment 136 and enters flexible segment 138 thereby deflecting segment 138 and repositioning the distal delivery opening of syringe barrel 132. As before, the transition of the syringe barrel portion 132 from its straight to a deflected condition can be tracked using the imagable markers denoting the relative positions of the sheath 134 and the syringe barrel segments 136 and 138, including by use of the transition marker 140 on the syringe barrel portion 132 and the distal markers 141 of sheath 134 which as depicted can include both a marker at the extreme distal end as well as a marker at the beginning of bend 144 and potentially markers therebetween. Also, as before, the distal delivery opening of the syringe barrel portion 132 can be repositioned either while distal segment 138 remains deflected and/or while distal segment 138 is returned to its generally straight or linear position by translating sheath 134 proximally along syringe barrel portion 132 and then rotating sheath 134, optionally with reference to visible marker 152 which indicates the direction of the bend 144. Plunger apparatus 26 can be actuated at appropriate times to deliver amounts of graft material 40 at one or more locations within the interbody space 32 and as necessary can be completely withdrawn to reload syringe barrel portion 32 with additional of graft material 40 to be delivered.

With reference now to FIGS. 14-17, shown is another embodiment of the present invention, generally wherein a syringe barrel is cooperable with a rod to control the position of the distal delivery opening of the syringe barrel. In particular, shown is syringe device 160 including syringe barrel portion 162 and control rod 164. Syringe barrel portion 162 includes a generally elongate body 166 having a control cannula 168 and a delivery lumen 170 extending longitudinally therethrough. Syringe barrel body 166 includes a bend 172 in a distal region thereof followed by a relatively straight distal segment 174 terminating a distal body end 176. Control cannula 168 includes a closed distal end 178 whereas delivery lumen 170 includes an open distal delivery end 180. Syringe barrel portion 162 further includes a collar 182 and a proximal open end 184 to control cannula 168. Syringe barrel portion 162 also includes a plurality of imagable distal segment markings 186 including one such marking located adjacent the bend 172. Control rod 164 includes an elongate body 188 having a distal end 190 which may be marked with an imagable marker 192, especially in instances where body 188 is made of a material which is not visible or poorly visible under the imaging system to be employed, e.g. where body 188 is made of a material that is generally non-radiopaque and an x-ray imaging technique will be used during surgery. On the other hand, where control rod body 188 is made from a radiopaque material such as a radiopaque metal, end marker 192 may not be necessary but can nonetheless be employed if greater visibility of the end is desired. Control rod 164 also includes a handle portion 194 connected to body 188.

Figure 14:
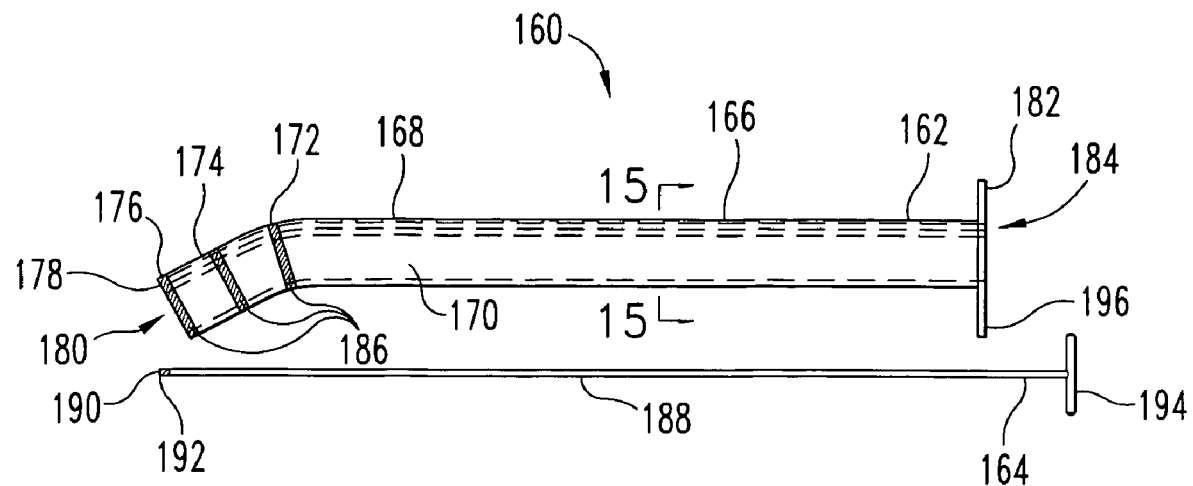
FIG. 14 illustrates a syringe device including a barrel and control rod cooperable to provide a straight configuration to an otherwise curved syringe barrel.
Figure 15:
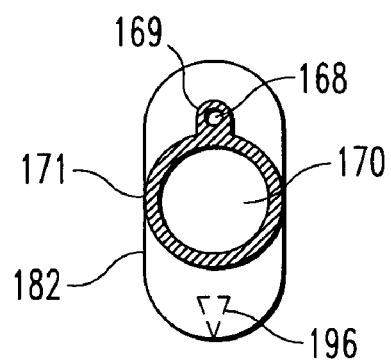
FIG. 15 provides cross-sectional view of the syringe barrel component depicted in FIG. 14 taken along section line 15-15 and viewed in the direction of the arrows.

With reference particularly to FIG. 15, shown is a cross-sectional view taken along section line 15-15 of FIG. 14 and viewed in the direction of the arrows. This view illustrates control cannula 168 and adjacent delivery cannula 170. As shown, these two cannulas can in certain embodiments be provided by an integral set of walls, for example by an extrusion process which forms both walls 169 defining control cannula 168 and walls 171 defining delivery lumen 170. In other embodiments, the cannulas can be provided by separate, attached pieces, for example. Also, shown in phantom is directional marker 196 occurring on the outer or proximal surface of collar 182 and which indicates the direction of bend 172 in the syringe barrel portion 162.

Figure 16:
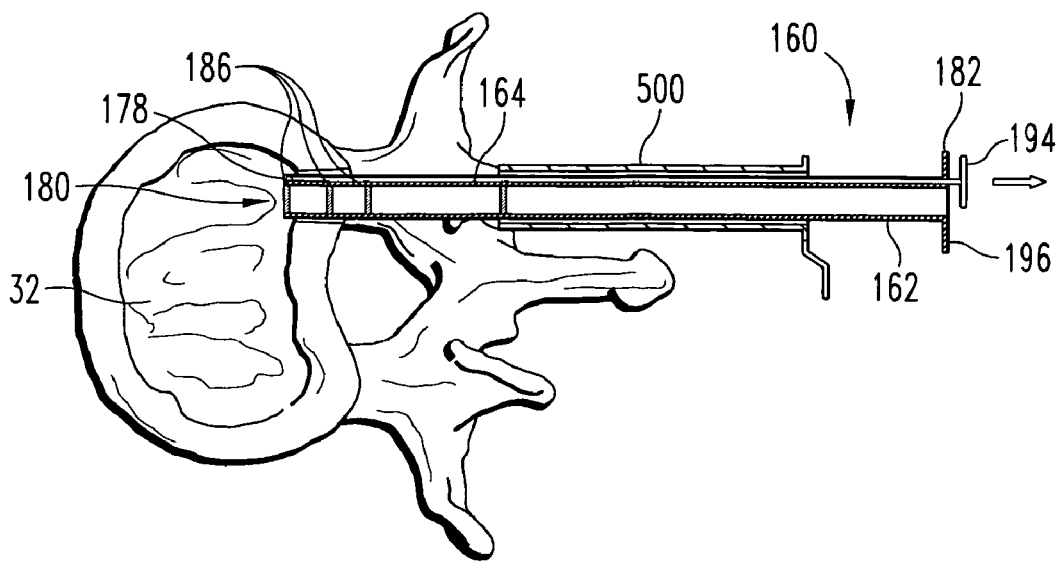
FIGS. 16 and 17 depict the apparatus of FIG. 14 in use.
Figure 17:
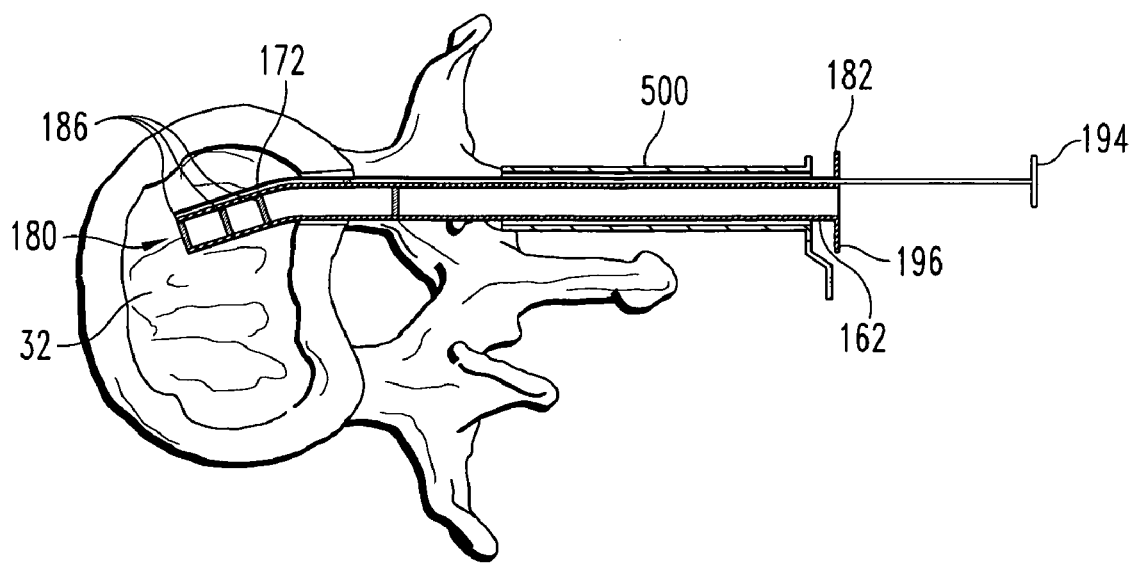
Figure 18:
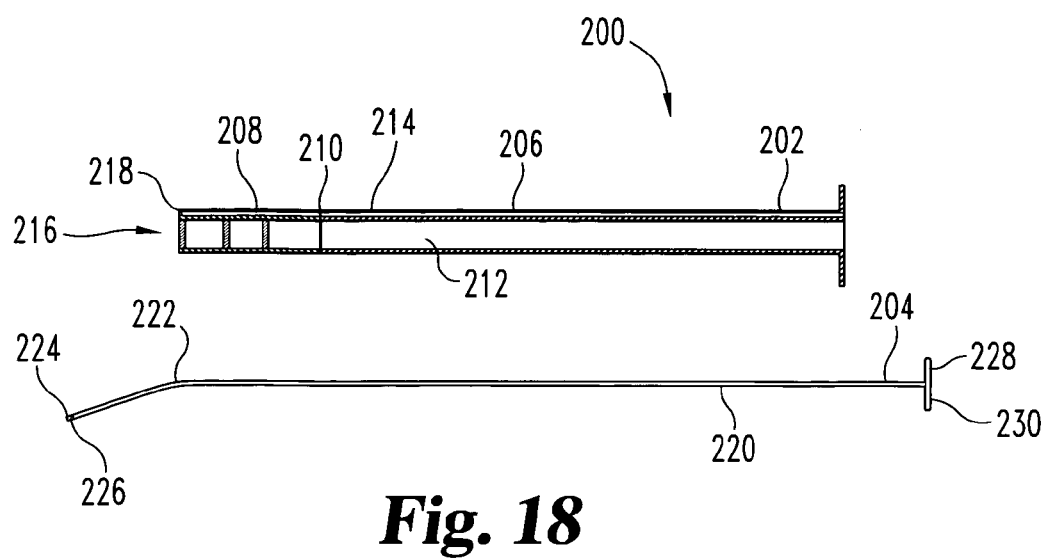
FIG. 18 illustrates syringe device of the invention having a barrel and control rod cooperable to deflect a distal region of an otherwise straight syringe barrel.
Figure 18A:
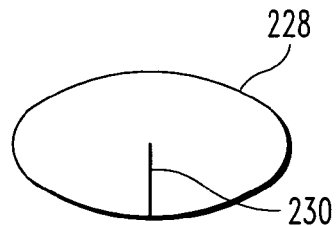
FIG. 18A provides a right end view of the control rod component depicted in FIG. 18.
Figure 19:
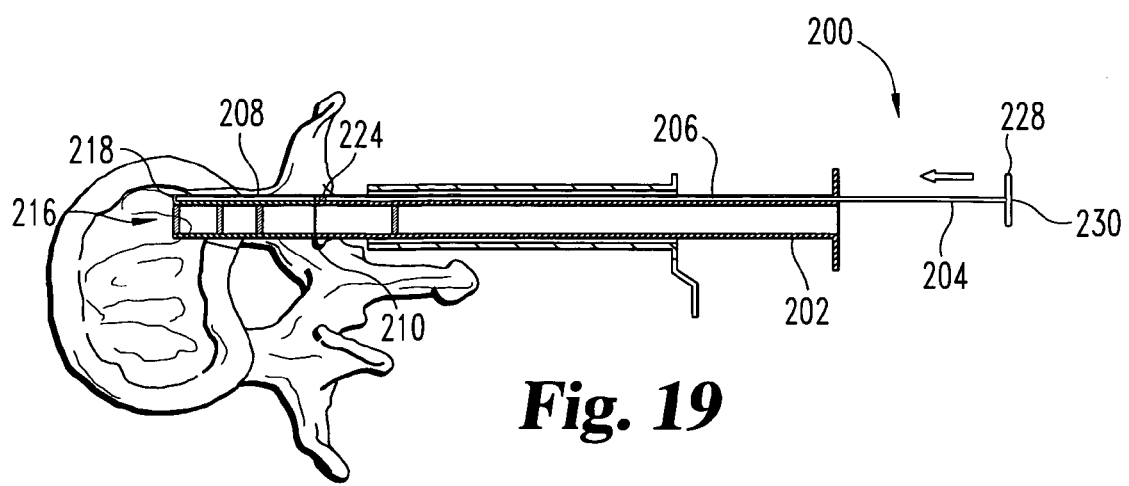
FIGS. 19-22 depict the apparatus of FIG. 18 in use.
Figure 20:
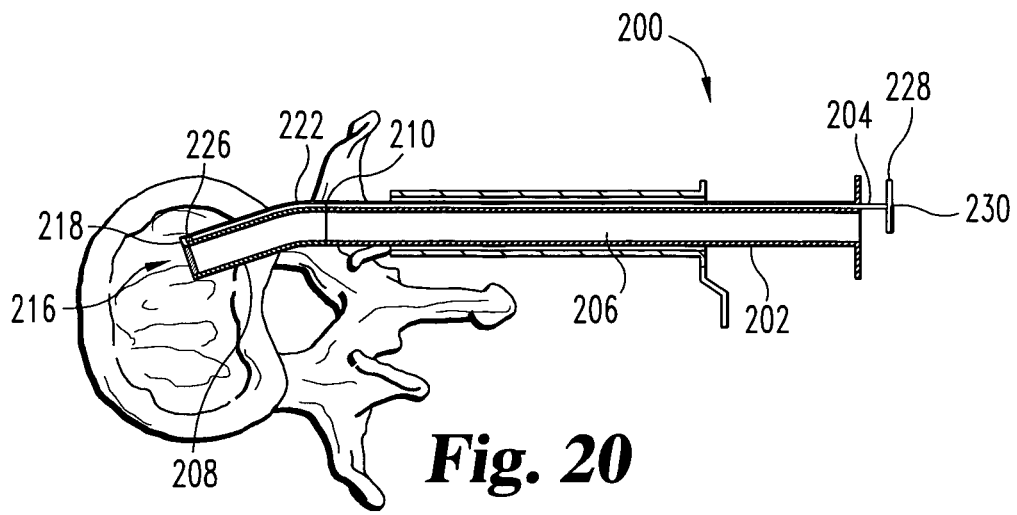
Figure 21:
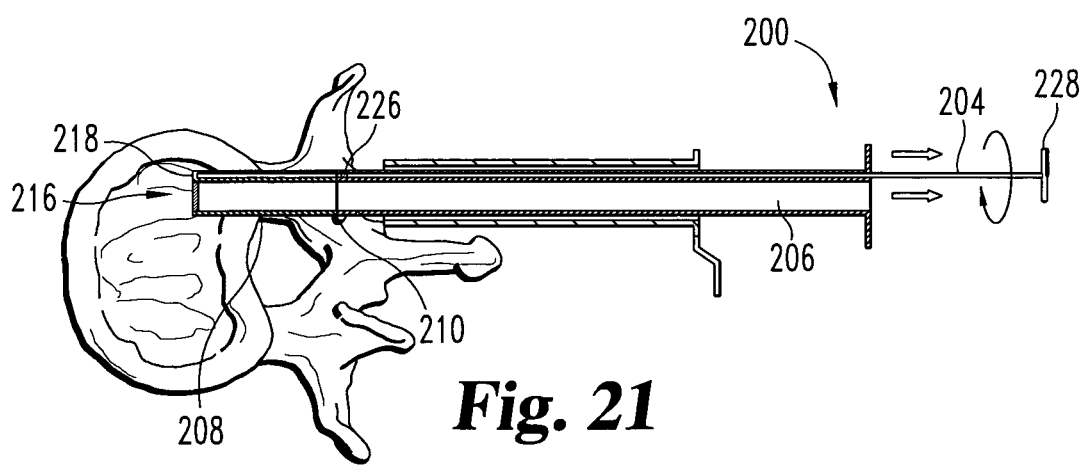
Figure 22:
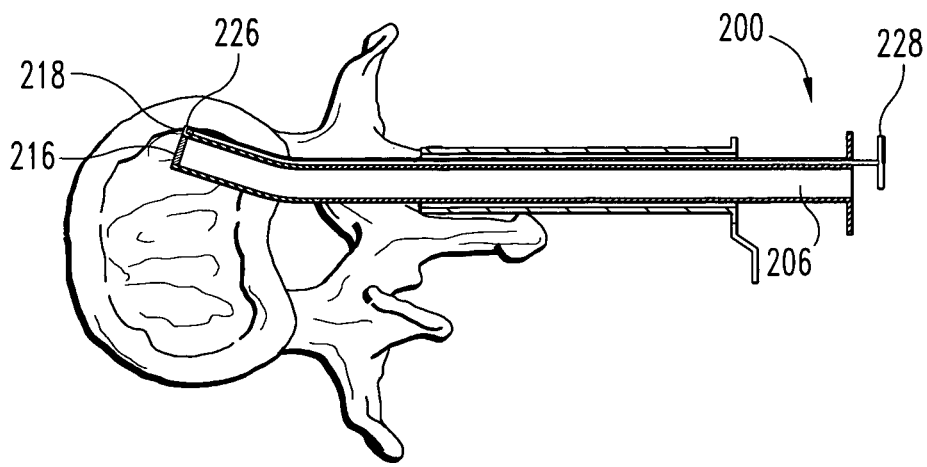

With reference now to FIGS. 16 and 17, in use, distal delivery opening 180 of device 160 can be advanced into an interbody space 32 with the device 160 in its overall straight configuration. This can be achieved with control rod 164 inserted completely within control cannula 168 so as to constrain bend 172 of syringe barrel portion 162 to a straight configuration, as shown. Thereafter, as depicted in FIG. 17, control rod 164 can be withdrawn proximally within control cannula 168 sufficiently to position tip 190 proximally of the transition between relatively stiff barrel portion 166 and relatively more flexible barrel portion 168, thus allowing bend 172 to achieve its relaxed configuration, repositioning distal delivery opening 180 more centrally within disc space 32. Thereafter, implant material can be delivered from the distal delivery opening 180 of syringe barrel portion 162 using a plunger or other material advancing mechanism. Furthermore, if repositioning of distal delivery opening 180 to another deflected position is desired, control rod 164 can be advanced so as to straighten bend 172, syringe barrel portion 162 rotated potentially with reference to visible indicia 196, and control rod 164 again withdrawn to allow bend 172 to return to its non-constrained curved condition thereby repositioning distal delivery opening 180 to a deflected position. Additional implant material can then be delivered.

With reference to FIGS. 18-22, another syringe device 200 and its use are illustrated. Syringe device 200 includes syringe barrel portion 202 and control rod 204. Syringe barrel portion 202 includes a generally stiff or rigid segment 206 and a more flexible segment 208, which flank a transition or dividing line between the segments marked by imagable marker band 210. Syringe barrel portion 202 includes a delivery lumen 212 and control lumen 214. Delivery lumen 212 has an open distal end 216, and control lumen 214 has a closed distal end 218. Control rod 204 includes an elongate body 220 having a bend or arcual portion 222 therein. Control rod 204 further has a distal tip 224, which can optionally include an imagable marker 226 the latter of which will be present especially in embodiments wherein control rod body 220 is made of a material that is otherwise not visible under the imaging system to be used. Control rod 204 further has a handle 228 which can include visible indicia 230 denoting the direction of bend 222. Control rod body 220 and rigid and flexible segments 206 and 208 are constructed such that rigid segment 206 has the capacity to straighten bend 222, and bend 222 has the capacity to deflect flexible segment 208. In use, syringe device 200 can be inserted to a desired location in its relatively straight configuration (see FIG. 19), whereafter control rod 204 with bend 222 therein can be advanced distally within syringe barrel portion 202 so as to achieve a deflected configuration (see e.g. FIG. 20) for delivery of graft material through distal delivery opening 216. When desired, control rod 204 can be withdrawn sufficiently to allow flexible segment 208 to return to its relatively straight configuration, rotated (see FIG. 21), and then advanced distally again so as to achieve a new deflected position for distal delivery opening 216 (see FIG. 22). Additional amounts of graft material can then be delivered.

In respect of syringe device 200 and other syringe devices disclosed herein with deflectable tips, it will be understood that in certain situations it may also be desirable to originally insert the syringe devices to an internal tissue area in a curved configuration, and thereafter deflect them to a straight or less curved configuration for delivery of an original amount of material or of additional amounts of material. Such embodiments are also contemplated as being within the present invention.

Figure 23:
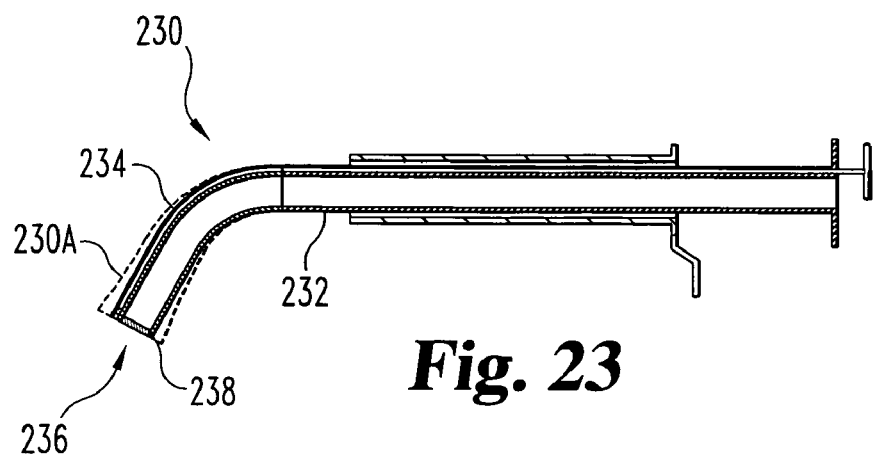
FIG. 23 depicts a syringe device of the invention having an alternative curved distal tip segment.

FIG. 23 depicts another syringe device 230 in accordance with the present invention, having an alternative curved distal tip configuration. Device 230 can be similar to any of the other syringe devices of the invention described herein, except having a more rounded bend portion 234 connected to a generally straight body 232. Device 230 can thus be used to deliver medical materials as described herein from its distal opening 236 and into an intervertebral space. Device 230 can also include an imagable marker 238 to mark the location of its distal tip. As well, as shown by the phantom or dotted lines of FIG. 23, a similar device 230A can include a taper extending outwardly toward its distal end to facilitate passage of graft materials, as described in connection with other tapered devices discussed above.

Figure 24:
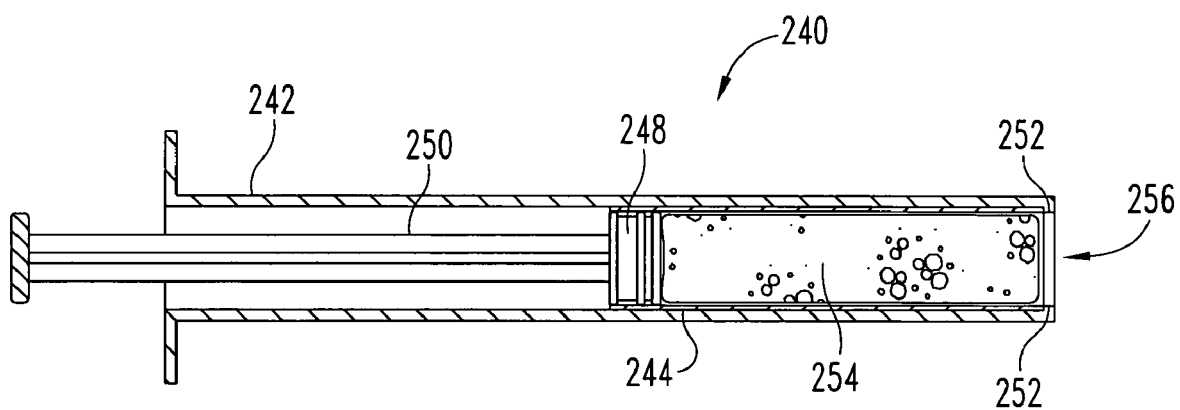
FIGS. 24 and 25 provide cross sectional and exploded perspective views, respectively, of another syringe device of the invention.
Figure 25:
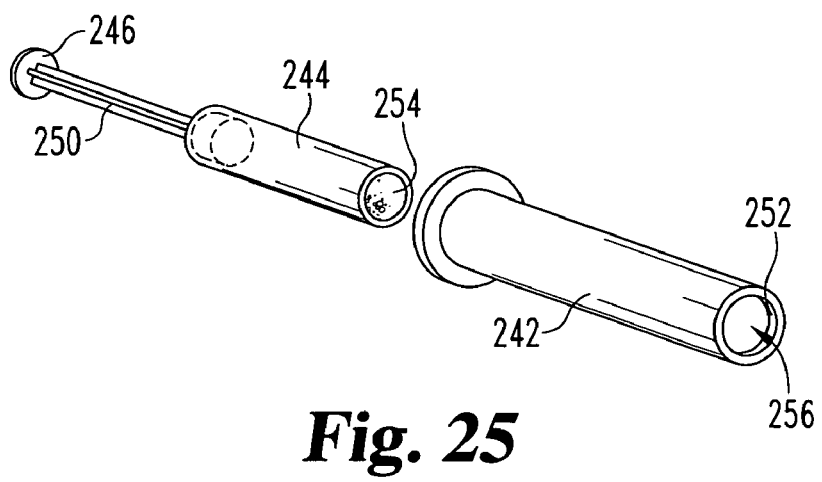

FIGS. 24 and 25 depict another syringe device 240 of the present invention. Device 240 includes an outer tubular syringe body 242, an inner tubular body 244, and a plunger apparatus 246 including a plunger head 248 and a plunger arm 250. Plunger apparatus 246 and inner tubular body 244 together form an assembly slidable within outer syringe body 242. Outer syringe body 242 includes internally-extending walls 252 at its distal tip forming a collar configured to act as a stop for inner tubular body 244 when inner body 244 has been inserted within and slidably advanced to the tip of outer syringe body 242. In this manner, with a graft material 254 received within inner tubular body 244, the plunger assembly 246/inner body 244 combination can be inserted within outer syringe body 242 and advanced until the distal tip of the inner body 244 contacts walls 252 to arrest advancement of the inner body 244. The advancement of inner body 244 can be achieved by pushing upon the proximal portion of the plunger apparatus 246.

In this regard, a number of arrangements can be used to prevent movement of the plunger head 248 within inner tubular body 244 during this movement through outer body 242, which would cause the graft material 254 to be deployed too early. Friction between the plunger head 248 and inner surfaces of the inner body 244 can be selected to prevent expulsion of the graft material during advance of the inner body 244 through the outer body 242. Upon impingement between the distal end of inner body 244 and stop walls 252, continued application of force to the plunger apparatus 246 will then cause expulsion of the graft material 252 from the distal opening 256 of the device 240.

In other arrangements, a mechanism for locking the relative position between the plunger mechanism 246 and the inner body 246 can be provided, and released only when the distal tip of inner body 244 reaches walls 252. Such mechanisms can include, for example, cooperation between features of the plunger arm 250 and a back wall provided upon inner body 244. One such cooperative arrangement may include cooperating threads provided on arm 250 and a hole in such a back wall, which can be disengaged by rotating the apparatus 246 to thereby release the position-locked condition and allow advancement of the apparatus 246 and in particular the plunger head 248 within the inner body 244. Other configurations to provide a twist-releasable lock between an inner body back wall and a plunger arm may also be used, including for instance a shaped hole in the back wall that can receive a proximal length of the plunger arm only when the plunger arm is rotated to a given position, for instance wherein the hole and the proximally-occurring plunger arm portion have generally corresponding, non-circular cross sections which can be misaligned to provide a locked condition, and aligned to allow advancement of the plunger arm and consequent expulsion of the graft material. Further, when such rotation-activated locking/unlocking mechanisms are employed, the distal end of the inner body 244 can optionally be configured to cooperate with features of the wall 252 to prevent undesired rotation of the body 244 as the plunger arm 250 is rotated. Such cooperation can include a friction-only arrangement but could also include cooperating tabs, pegs/holes, interleaving portions, etc. to prevent rotation of the inner body 244 when received against the stop 252.

In other embodiments of the invention, the inner body 244 can be or include an extension of such a length that a portion thereof extends out of the proximal end of outer body 244 when the distal tip of body 244 is received against stop wall 252. In this manner, force can be applied to the inner body 244 or its extension (rather than to plunger apparatus 246) to advance the body 244 completely to the tip of outer body 242, whereafter plunger apparatus 246 can be operated to expel the graft material 254 out of distal opening 256.

In still other embodiments, inner tubular member 244 and/or outer tubular member 242 could be configured such that advancement of inner member 244 is stopped only after a portion of member 244 has exited distal opening 256, thus providing a telescoping arrangement. Thereafter, plunger apparatus 246 could be actuated to dispense the medical material. Such telescoped stop arrangements can be provided in any suitable manner, including for example a change in the outer diameter (O.D.) of the inner member 244 whereupon impingement of the walls 252 occurs only after a smaller O.D. portion of the inner member 244 has exited opening 256, or a similar larger-O.D. flange or collar occurring along the length of inner member 244 to impinge upon walls 252 after a telescoping arrangement has been achieved. These and other suitable cooperative stop telescoping arrangements can be used within the scope of the present invention.

Figure 26:
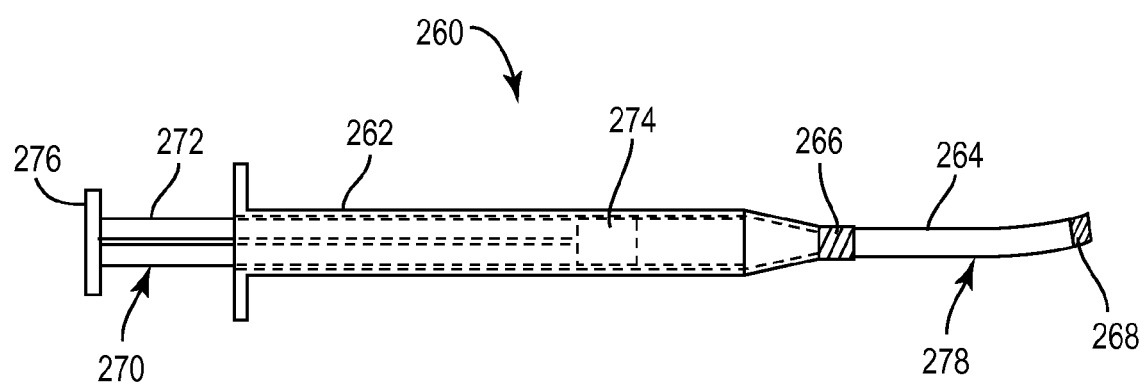
FIG. 26 depicts a syringe device of the invention having a syringe barrel and a distally-attached flexible tube.

FIG. 26 depicts another syringe device of and for use in aspects of the present invention. Syringe device 260 includes a syringe barrel 262 and a flexible tube 264 attached to the distal end of the barrel 262, for example by cooperating threaded attachment 266. Flexible tube 264 includes an imagable (e.g. radiopaque) marker 268 adjacent the distal end thereof for purposes of positional monitoring. Device 260 also includes a plunger assembly 270 including a plunger arm 272, a plunger head 274, and a plunger push-plate 276. Flexible tube 264 preferably has or is conformable to provide a bend 278 for directional delivery of an osteogenic material to an interbody space. In use, device 260 can be loaded with a transferable osteogenic material as described herein and used to deliver the material from within barrel portion 262 through tube 264 and into the interbody space. Such material deliveries can be used in the conduct of any suitable fusion procedure, including guide tube assisted or otherwise cannulated minimally-invasive procedures. In certain such inventive procedures, the syringe barrel portion 262 can be advanced into the guide tube (e.g. 500, see other FIGs.), but can remain external of the interbody space. Instead, the more flexible tube 264 can extend into the disc space for delivery of the osteogenic material, during which marker band 268, when present, can be used to monitor its position. It will be understood that in alternative embodiments the more flexible tube 264 can have an internal and/or external diameter that is/are smaller than, the same as, or larger than the corresponding internal and/or external diameter of the syringe barrel portion 262. In addition, the internal diameters of the syringe barrel portion 262 and/or of the tube 264 can vary along their length, including for example one or both of them having an internal diameter that increases in the distal direction, with the increasing dimension optionally terminating at their distal ends.

In certain embodiments, syringe devices of the invention are adapted particularly for use in delivering materials in a minimally invasive surgical procedure to an interbody space between spinal vertebrae, especially in a human. Such syringe devices will typically have inner diameters ranging from about 3 mm to about 14 mm and outer diameters ranging from about 4 mm to about 15 mm. In certain inventive embodiments, such syringe devices will have inner diameters of about 3 mm to about 8 mm, and outer diameters of about 4 mm to about 9 mm. As to lengths, such syringe devices will typically have lengths of about 5 cm to about 50 cm. Illustratively, advantageous syringe devices for posterior surgical approaches to the human interbody space can have lengths of about 5 to about 25 cm, whereas advantageous syringe devices for anterior surgical approaches to the human interbody space can have lengths of about 20 cm to about 50 cm.

Syringe devices of the present invention are useful in the practice of minimally-invasive spinal fusion procedures, including those involving anterior surgical approaches, e.g. using laproscopic instrumentation, and those involving posterior surgical approaches, e.g. using introducer sleeves. Suitable Minimal Spinal Access Technology (MAST) products for these types of procedures are available, for example, from Medtronic Sofamor Danek, Inc. (Memphis, Tenn.), including for instance the METRx™ X-Tube™ retraction system.

Generally in minimally invasive approaches, surgical access is provided to the interbody space through the cannulated device (e.g. laproscope or sleeve). In one specific example, minimally invasive posterior access can be provided by a procedure that includes positioning of a cannulated device such as the X-Tube™ within soft patient tissues, e.g. after incision and passage of a series of tissue dilators of increasing size to create an opening for the cannulated device. Oftentimes, a laminectomy is performed, in which at least a portion of the lamina will be excised from a vertebra occurring above the disc space to be accessed. Potentially also, the procedure can involve excision of at least a portion of an articular facet (facetectomy) or other bony structures as necessary for surgical access. After access to the disc space is gained, patient disc tissue can be excised, the vertebral endplates can be decorticated using minimally invasive instrumentation therefor, and one or more loadbearing implants such as cages or bone spacers can be introduced through the cannulated device. In accordance with the embodiments of the present invention, medical material such as an osteogenic material can be introduced into the disc space before and/or after placement of such loadbearing implant(s), using a syringe device as described herein.

In certain aspects of the invention, syringe devices as described herein can also be used to deliver medical material to other surgical sites, particularly sites at which bone growth is desired. These include, for instance, the repair of cranial defects, iliac crest back-filling, acetabular defects, and in the repair of tibial plateau and long bone defects. Such syringe-based delivery can be used to treat major or minor defects in these or other bones caused by trauma (including open and closed fractures), disease, or cogenital defects, for example.

As stated above, materials delivered and dispensed by the various syringe device embodiments and methods of the present invention can be various types of implant materials as would generally occur to one skilled in the art. In this regard, carriers that may be used in the implant materials can be dimensionally-stable or non-dimensionally-stable (e.g. liquid or paste) carriers. The carrier can, for example, comprise a resorbable porous matrix.

In this regard, the resorbable porous matrix is collagenous in certain embodiments. A wide variety of collagen materials are suitable for the resorbable matrix. Naturally occurring collagens may be subclassified into several different types depending on their amino acid sequence, carbohydrate content and presence or absence of disulfide cross-links. Types I and III collagen are two of the most common subtypes of collagen. Type I collagen is present in skin, tendon and bone whereas Type III collagen is found primarily in skin. The collagen in the matrix may be obtained from skin, bone, tendon, or cartilage and purified by methods known in the art. Alternatively, the collagen may be purchased commercially. The porous matrix composition desirably includes Type I bovine collagen.

The collagen of a carrier matrix can further be atelopeptide collagen and/or telopeptide collagen. Moreover, non-fibrillar and/or fibrillar collagen may be used. Non-fibrillar collagen is collagen that has been solubilized and has not been reconstituted into its native fibrillar form.

Suitable resorbable carrier matrix materials may also be formed of other organic materials such as natural or synthetic polymeric materials, in addition to or as an alternative to collagen. For example, the resorbable carrier may comprise gelatin (e.g. foamed gelatin), or resorbable synthetic polymers such as polylactic acid polymers, polyglycolic acid polymers, or co-polymers thereof. Other natural and synthetic polymers are also known for the formation of biocompatible resorbable matrix materials, and can be used in the invention.

The carrier may also be or include a natural and/or synthetic mineral component. For example, the mineral component can be provided by a particulate mineral material, including either powder form or larger particulate mineral materials. In certain embodiments, the particulate mineral component is effective in providing a scaffold for bone ingrowth as the resorbable matrix material is resorbed. The mineral material may for example be bone, especially cortical bone, or a synthetic bioceramic such as a biocompatible calcium phosphate ceramic. Illustrative ceramics include tricalcium phosphate, hydroxyapatite, and biphasic calcium phosphate. These mineral components may be purchased commercially or obtained or synthesized by methods known in the art.

As noted above, biphasic calcium phosphate can be used to provide a mineral-containing carrier in the invention. Desirably, such biphasic calcium phosphate will have a tricalcium phosphate:hydroxyapatite weight ratio of about 50:50 to about 95:5, more preferably about 70:30 to about 95:5, even more preferably about 80:20 to about 90:10, and most preferably about 85:15.

The carrier can include an amount of mineral that will provide a scaffold effective to remain in a patient for a period of time sufficient for the formation of osteoid in the void for which bone growth is desired. The minimum level of mineral that must be present in the carrier for these purposes is also dependent on the level of activity of the tissue growth promoting components in the isolate and whether other substances such as BMP or other osteogenic proteins are incorporated into the carrier in combination with the tissue growth promoting components of the isolate.

In certain forms of the invention, the carrier may include a particulate mineral component embedded in a porous organic matrix formed with a material such as collagen, gelatin or a resorbable synthetic polymer. In this regard, the particulate mineral:resorbable porous matrix weight ratio of the first implant material may be at least about 4:1, more typically at least about 10:1. In highly mineralized carriers, the particulate mineral will constitute at least 95% by weight of the first implant material. For example, carrier materials may be provided comprising about 97% to about 99% by weight particulate mineral and about 1% to about 3% of the collagen or other matrix forming material. Moreover, the mineral component may for example have an average particle size of at least about 50 microns, more preferably about 0.5 mm to about 5 mm, and most preferably about 1 mm to about 3 mm.

Carriers used may be non-dimensionally-stable, for example as in flowable or malleable substances such as liquids or pastes. Illustratively, the carrier may include a biologically resorbable, non-dimensionally-stable material having properties allowing its implantation and retention at a tissue defect site. Such carriers can include resorbable organic materials such as macromolecules from biological or synthetic sources, for example gelatin, hyaluronic acid carboxymethyl cellulose, collagen, peptides, glycosaminoglycans, proteoglycans, and the like. Such materials can be used with or without an incorporated particulate mineral component as described hereinabove. In certain forms, the resorbable carrier can be formulated into the composition such that the composition is flowable at temperatures above the body temperature of a patient into which the material is to be implanted, but transitions to be relatively non-flowable at or slightly above such body temperature. The resorbable carrier may be formulated into the implanted composition so the flowable state is a liquid or a flowable gel, and the non-flowable state is a stable gel or solid. In certain embodiments of the invention, the resorbable carrier can include gelatin, and/or can incorporate a particulate mineral in an amount that constitutes about 20% to about 80% by volume of the carrier composition, more typically about 40% to about 80% by volume.

In addition to the carrier, the implant material can comprise growth factors which can modulate the growth or differentiation of other cells. Growth factors which can be used include, but are not limited to, bone morphogenic proteins, sMAD proteins, and LIM mineralization proteins. Demineralized bone matrix can also be included in the carrier. For example, powders or granules of demineralized bone matrix can be incorporated into the carrier.

As noted above, implant materials used in the invention can incorporate an osteogenic protein carried by the implant carrier material, for example received upon and/or within the carrier material, either in a dry form that can be delivered or in a liquid formulation retained by the carrier or mixed with the carrier. For example, the osteogenic protein can be a BMP. Recombinant human BMPs can be used, and may be commercially obtained or prepared as described and known in the art, e.g. in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al. The osteogenic protein may be isolated from tissue sources such as bone. Methods for isolating BMP from bone are described, for example, in U.S. Pat. No. 4,294,753 to Urist and Urist et al., PNAS 371, 1984.

Bone morphogenic proteins useful in the invention will include proteins comprising any of the native polypeptide chains, whether isolated from naturally-occurring sources, or produced by recombinant DNA or other synthetic techniques, and includes allelic and phylogenetic counterpart variants of these proteins, as well as muteins thereof, and various truncated and fusion constructs. Deletion or addition mutants also are envisioned to be active, including those that may alter the conserved C-terminal cysteine domain, provided that the alteration does not functionally disrupt the relationship of these cysteines in the folded structure. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The bone morphogenic proteins contemplated for use herein can be expressed from intact or truncated cDNA or from synthetic DNAs in prokaryotic or eukaryotic host cells, and purified, cleaved, refolded, and dimerized to form morphogenically active compositions. Candidate host cells include, without limitation, prokaryotes including $E.\ coli$, or eukaryotes including yeast, or mammalian cells, such as CHO, COS or BSC cells. One of ordinary skill in the art will appreciate that other host cells can be used to advantage. Detailed descriptions of specific bone morphogenic proteins useful in the practice of this invention, including how to make, use and test them for osteogenic activity, are disclosed in numerous publications, including for example those referenced hereinabove. Additional osteogenic proteins that may be used in aspects of the present invention are included in the class of osteogenic proteins identified in U.S. patent application Ser. No. 09/045,331 filed Mar. 20, 1998, published Aug. 23, 2001 as US 20010016646 A1, which is hereby incorporated herein by reference in its entirety and particularly with respect to its identification of osteogenic proteins.

The osteogenic proteins or other biologically active agents to be used in the present invention can be delivered in certain embodiments as liquid formulations, for example aqueous formulations, which are mixed with, received upon and/or within, or otherwise combined with carrier materials as discussed above. In certain specific embodiments, the osteogenic protein formulation or other medical formulation will be provided as a liquid formulation which is received within the pores of a compressible carrier material. The compressible carrier material can be a generally three-dimensionally-stable body material such as a spongiform material which may or may not exhibit shape memory after compression, e.g., in the latter case exhibiting properties consistent with a stiff porous putty which is subject to deformation, especially when wet, that compresses the pores of the material. In other embodiments, the carrier can be a non-three-dimensionally-stable carrier material such as a paste. In any of these embodiments, the application of force to the carrier material can compress the material and cause liquid formulation received therein to separate from the carrier material, for example by expressing the liquid formulation from the internal spaces which are compressed. As discussed generally above, syringe devices and methods of the invention can be used with advantage when delivering such implant materials to patients, as they facilitate the advancement of the compressible carrier material through the delivery lumen of the syringe barrel with minimal or no compression whereby expression of the liquid formulation from pores of the compressible material is minimized or prevented.

In embodiments as discussed above wherein a liquid formulation is received within a compressible carrier material, the liquid formulation can be combined with the carrier material in any suitable manner and at any suitable point during manufacture or in the surgical field. For example, in certain embodiments a surgeon or other health care provider can apply a liquid formulation of a medical agent onto and into the carrier material prior to implant by soaking, spraying or otherwise. In other embodiments, the carrier material in dry form may include dried amounts of the medical agent, and can thereafter be wetted whereupon liquid within pores of the carrier material will contain dissolved or suspended amounts of the medical agent. In either case, this liquid formulation-containing compressible carrier material can be loaded into syringe devices of the present invention and delivered to desired implant locations such as the interbody space between adjacent vertebra.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents and patent applications cited in this specification are herein incorporated by reference as if each individual publication, patent or patent application was specifically and individually indicated to be incorporated by reference as set forth in its entirety herein.

What is claimed is:

1. A syringe device for delivering an osteogenic material to an interbody space between first and second adjacent vertebra of a patient, the device comprising:
   (a) an elongate syringe barrel having a rigid portion and an internal lumen communicating with an open distal end, said open distal end receivable within an interbody space between first and second adjacent vertebra of a patient, the open distal end having a deflectable region, the deflectable region being flexible and having a marker, wherein in a direction extending toward said open distal end there is a tapered region of increasing diameter that begins at or just after a curved portion;
   (b) a porous osteogenic material received in the lumen of said elongate syringe barrel and having a trailing end; said porous osteogenic material incorporating a liquid pharmaceutical composition comprising an osteogenic protein, said liquid pharmaceutical composition captured within pores of a porous carrier material; said porous carrier material further being compressible, wherein compression of the carrier material expels amounts of said liquid pharmaceutical composition out of said pores such that the liquid pharmaceutical composition escapes the porous carrier material;
   (c) a plunger configured to move in the lumen and apply force to the trailing end of the porous osteogenic material to advance the material through the lumen of the syringe barrel, the plunger being rigid and less flexible than the deflectable region and having a bend portion to deflect the deflectable region of the syringe barrel and an imagable marker that marks the bend portion; and wherein said syringe barrel, plunger and porous osteogenic material are configured wherein the porous osteogenic material is advanceable through the internal lumen with said plunger without substantial compression of the porous osteogenic material which thereby retains the liquid pharmaceutical composition.

2. The syringe device of claim 1, wherein said osteogenic protein is a bone morphogenic protein.

3. A syringe device useful for delivering a medical substance, the device comprising:
   an elongate, needleless syringe barrel with a rigid portion and a distal barrel end having a deflectable region, the deflectable region being flexible and the distal end having a distal delivery opening, said syringe barrel having an internal lumen, wherein in a direction extending toward a distal open end there is a tapered region of increasing diameter that begins at or just after a curved portion;
   a pushing element configured to advance in the lumen and having a leading end for contacting and advancing a medical substance through the lumen of the syringe barrel and out the distal delivery opening, the pushing element being rigid and less flexible than the deflectable region and having a bend portion to deflect the deflectable region of the syringe barrel; and
   an imagable marker on said syringe barrel at the deflectable region and said pushing element at the bend portion.

4. The syringe device of claim 3, wherein said imagable marker is a radiopaque marker.

5. The syringe device of claim 3, configured for delivery of an osteogenic material to an interbody space between first and second adjacent vertebra of a patient.

6. A syringe device useful for delivering a medical substance, the device comprising:
   an elongate syringe barrel having an internal lumen, a proximal region and a distal region, the proximal region comprising a rigid portion, the distal region comprising a deflectable portion, the deflectable portion being flexible and having a marker, wherein in a direction extending toward a distal open end there is a tapered region of increasing diameter that begins at or just after a curved portion;
   at least one element cooperable with said syringe barrel to selectively introduce and remove a curvature in at least a portion of said syringe barrel; and
   a plunger configured to move within the lumen and advance a medical substance through the lumen of the syringe barrel, the plunger being rigid and less flexible than the deflectable portion and having a bend portion to deflect the deflectable portion of the syringe barrel and an imagable marker to mark the bend portion.

7. The syringe device of claim 6, wherein said at least one element comprises a sheath.

8. The syringe device of claim 6, wherein said at least one element comprises a rod.

9. The syringe device of claim 8, wherein said syringe barrel includes a first lumen for delivery of the medical substance and a second lumen for receipt of the rod.

10. The syringe device of claim 9, wherein said syringe barrel has a straight configuration when in a relaxed condition.

11. The syringe device of claim 9, wherein said syringe barrel has a curved configuration when in a relaxed condition.

12. The syringe device of claim 10, wherein said rod has a curved configuration when in a relaxed condition.

13. The syringe device of claim 11, wherein the rod has a straight configuration when in a relaxed condition.

14. The syringe device of claim 7, wherein said sheath has a curved configuration when in a relaxed condition.

15. The syringe device of claim 7, wherein said sheath has a straight configuration when in a relaxed condition.

16. The syringe device of claim 14, wherein said syringe barrel has a straight configuration when in a relaxed condition.

17. The syringe device of claim 15, wherein said syringe barrel has a curved configuration when in a relaxed condition.

18. A syringe device useful for delivering a medical graft material susceptible to compression, comprising:
   a syringe barrel including a proximal end and a distal end; said syringe barrel including at least a barrel segment configured for passage of the medical graft material, said barrel segment including an internal lumen terminating in a distal delivery opening, said internal lumen including at least a portion widening in a direction toward said distal delivery opening, and wherein the delivery opening has a delivery opening cross-sectional area at least as great as a minimum cross-sectional area of said barrel segment, the proximal end comprising a rigid portion, the distal end comprising at least one deflectable portion, the deflectable portion being flexible and having a marker, wherein the syringe barrel comprises threads; and
   a plunger mechanism configured to move within the internal lumen and within said barrel segment and effective to transfer the medical material through said internal lumen and out of said delivery opening, the plunger mechanism being rigid and less flexible than the deflectable portion and having a bend portion to deflect the deflectable portion of the syringe barrel and an imagable marker to mark the bend portion, wherein the plunger is configured to cooperate with the threads of the syringe barrel.

19. The syringe device of claim 18, wherein said widening occurs in one or more steps along the length of said barrel.

20. The syringe device of claim 18, further comprising a funnel segment extending from said proximal end of said barrel.

21. The syringe device of claim 18, wherein said widening is continuous.

22. The syringe device of claim 18, configured for delivery of a medical substance to a spinal interbody space of a patient.

23. A syringe assembly useful for delivering an implant material, comprising:
   a syringe barrel having an internal lumen, said barrel including a distal barrel end providing a distal delivery opening, and a proximal barrel end, said barrel further including an arcual portion proximal to said distal end, the proximal barrel end comprising a rigid portion, the distal barrel end comprising at least one deflectable portion, the deflectable portion being flexible and having a marker, wherein the syringe barrel comprises threads;
   said lumen including one or more regions of increasing cross-sectional area extending in a direction toward said distal barrel end;
   the delivery opening having a delivery opening cross-sectional area at least as great as a minimum cross-sectional area along the length of the syringe barrel; and
   a material pushing element configured to move within the lumen and operable to move the material through said lumen toward the distal end of said barrel, the material pushing element being rigid and less flexible than the deflectable portion and having a bend portion to deflect the deflectable portion of the syringe barrel and an imagable marker to mark the bend portion, wherein the plunger is configured to cooperate with the threads of the syringe barrel.

24. The syringe assembly of claim 23, further comprising a funnel segment configured for receipt of the implant material and extending from said proximal end of said barrel.

25. An apparatus useful for dispensing a medical material, comprising:
- a syringe barrel having an internal lumen, said barrel including a receiving portion, a dispensing portion, and a central portion connecting said receiving portion and said dispensing portion, wherein said central portion has a rigid portion and said dispensing portion includes an arcual shape and at least one deflectable portion, the deflectable portion being flexible and having a marker, wherein the syringe barrel comprises threads and
- a material moving element configured to move within the lumen and translatable within said barrel to move the material toward said dispensing portion, wherein said material moving element being rigid and less flexible than the deflectable portion and having a bend portion to travel within at least a part of said arcual shape of the dispensing portion and deflect the at least one deflectable portion of the syringe barrel and an imagable marker to mark the bend portion, wherein the plunger is configured to cooperate with the threads of the syringe barrel.

26. The apparatus of claim 25, wherein said material moving element includes one or more guides circumferentially disposed about said element to guide said material moving element through said internal chamber of said syringe barrel.

27. The apparatus of claim 25, wherein said receiving portion has a funnel shape with a cross-sectional diameter decreasing toward said central portion.

28. The apparatus of claim 25, wherein said lumen has one or more regions of increasing cross-sectional area.

29. The apparatus of claim 28 further comprising a sheath body, wherein one segment of the syringe barrel that flanks a bend portion is made of a material that is not deflectable by the sheath and the bend portion that is made of a material that is capable of deflection by the sheath body.

* * * * *

UNITED STATES PATENT AND TRADEMARK OFFICE
CERTIFICATE OF CORRECTION

PATENT NO. : 8,092,464 B2
APPLICATION NO. : 11/120135
DATED : January 10, 2012
INVENTOR(S) : McKay It is certified that error appears in the above-identified patent and that said Letters Patent is hereby corrected as shown below:

In Column 18, Line 34, delete "Minimal Spinal Access Technology (MAST)" and insert
-- Minimal Access Spinal Technology (MAST) --, therefor.

Signed and Sealed this
Tenth Day of April, 2012

David J. Kappos
*Director of the United States Patent and Trademark Office*